(12) United States Patent
Greene et al.

(10) Patent No.: US 9,585,946 B2
(45) Date of Patent: *Mar. 7, 2017

(54) COMPOSITIONS AND METHODS COMPRISING GLYCYL-TRNA SYNTHETASES HAVING NON-CANONICAL BIOLOGICAL ACTIVITIES

(71) Applicant: aTyr Pharma, Inc., San Diego, CA (US)

(72) Inventors: Leslie Ann Greene, San Diego, CA (US); Ryan Andrew Adams, San Diego, CA (US); Fei Hong, San Diego, CA (US); Ji Zhao, San Diego, CA (US); Eva Rebecka Stephanie Armour, San Diego, CA (US); Kristi Helen Piehl, San Diego, CA (US)

(73) Assignee: aTyr Pharma, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/844,666

(22) Filed: Sep. 3, 2015

(65) Prior Publication Data

US 2016/0114016 A1  Apr. 28, 2016

Related U.S. Application Data

(63) Continuation of application No. 14/262,247, filed on Apr. 25, 2014, now Pat. No. 9,157,076, which is a continuation of application No. 13/753,272, filed on Jan. 29, 2013, now Pat. No. 8,747,840, which is a continuation of application No. 12/492,925, filed on Jun. 26, 2009, now Pat. No. 8,404,471.

(60) Provisional application No. 61/095,548, filed on Sep. 9, 2008, provisional application No. 61/076,098, filed on Jun. 26, 2008.

(51) Int. Cl.

| | |
|---|---|
| *C12N 9/00* | (2006.01) |
| *C12N 15/00* | (2006.01) |
| *C12P 21/06* | (2006.01) |
| *C12P 21/04* | (2006.01) |
| *A61K 38/43* | (2006.01) |
| *A61K 38/53* | (2006.01) |
| *C12N 9/96* | (2006.01) |
| *C07K 1/14* | (2006.01) |
| *C12N 15/10* | (2006.01) |

(52) U.S. Cl.
CPC .............. *A61K 38/53* (2013.01); *C07K 1/14* (2013.01); *C12N 9/93* (2013.01); *C12N 9/96* (2013.01); *C12N 15/102* (2013.01); *C12Y 601/01014* (2013.01)

(58) Field of Classification Search
CPC ....................................................... C12N 9/93
See application file for complete search history.

(56) References Cited

U.S. PATENT DOCUMENTS

| | | |
|---|---|---|
| 6,225,060 B1 | 5/2001 | Clark et al. |
| 6,428,960 B1 | 8/2002 | Clark et al. |
| 6,548,060 B1 | 4/2003 | Kim |
| 6,743,619 B1 | 6/2004 | Tang et al. |
| 6,903,189 B2 | 6/2005 | Schimmel et al. |
| 7,067,126 B2 | 6/2006 | Schimmel et al. |
| 7,144,984 B2 | 12/2006 | Schimmel et al. |
| 7,196,068 B2 | 3/2007 | Kim et al. |
| 7,273,844 B2 | 9/2007 | Schimmel et al. |
| 7,413,885 B2 | 8/2008 | Schimmel et al. |
| 7,459,529 B2 | 12/2008 | Kim |
| 7,476,651 B2 | 1/2009 | Schimmel et al. |
| 7,521,215 B2 | 4/2009 | Schimmel et al. |
| 7,528,106 B2 | 5/2009 | Friedlander et al. |
| 7,901,917 B2 | 3/2011 | Schimmel et al. |
| 7,902,165 B2 | 3/2011 | Kim |
| 8,003,780 B2 | 8/2011 | Kim et al. |
| 8,017,593 B2 | 9/2011 | Schimmel et al. |
| 8,026,088 B2 | 9/2011 | Yang |
| 8,101,566 B2 | 1/2012 | Schimmel et al. |
| 8,148,125 B2 | 4/2012 | Schimmel et al. |
| 8,404,242 B2 | 3/2013 | Zhou et al. |
| 8,404,471 B2 | 3/2013 | Greene et al. |
| 8,747,840 B2 | 6/2014 | Greene et al. |
| 2002/0182666 A1 | 12/2002 | Schimmel et al. |
| 2003/0017564 A1 | 1/2003 | Schimmel et al. |
| 2003/0215827 A1 | 11/2003 | Yue et al. |
| 2004/0018505 A1 | 1/2004 | Lee et al. |
| 2004/0048290 A1 | 3/2004 | Lee et al. |
| 2004/0101879 A1 | 5/2004 | Seidel-Dugan et al. |
| 2004/0152079 A1 | 8/2004 | Schimmel et al. |
| 2006/0024288 A1 | 2/2006 | Glidden |

(Continued)

FOREIGN PATENT DOCUMENTS

| | | |
|---|---|---|
| CN | 1341725 | 3/2002 |
| CN | 1341727 | 3/2002 |

(Continued)

OTHER PUBLICATIONS

Ge et al. Primary structure and functional expression of human Glycyl-tRNA synthetase, an autoantigen in myositis. J Biol Chem. Nov. 18, 1994;269(46):28790-7.*
Office Action for U.S. Appl. No. 12/492,925, mailed on Jan. 6, 2012.
Office Action for U.S. Appl. No. 12/492,925, mailed on Jun. 11, 2012.
International Preliminary Report on Patentability for International Application No. PCT/US2009/048915, dated Jan. 5, 2011.
International Search Report and Written Opinion for International Application No. PCT/US2009/048915, mailed Nov. 2, 2009.
Office Action for U.S. Appl. No. 13/753,272, mailed on Jul. 19, 2013.
Office Action for U.S. Appl. No. 12/482,151, mailed Oct. 11, 2011.
Office Action for U.S. Appl. No. 12/482,151, mailed Mar. 18, 2011.

(Continued)

*Primary Examiner* — Yong Pak
(74) *Attorney, Agent, or Firm* — Cooley LLP

(57) ABSTRACT

Isolated glycyl-tRNA synthetase polypeptides and polynucleotides having non-canonical biological activities are provided, as well as compositions and methods related thereto.

19 Claims, 21 Drawing Sheets

(56) References Cited

U.S. PATENT DOCUMENTS

| | | |
|---|---|---|
| 2006/0046250 A1 | 3/2006 | Kim |
| 2006/0078553 A1 | 4/2006 | Glidden |
| 2007/0048322 A1 | 3/2007 | Schimmel et al. |
| 2007/0061916 A1 | 3/2007 | Kovalic et al. |
| 2007/0111238 A1 | 5/2007 | Jamieson et al. |
| 2009/0227002 A1 | 9/2009 | Schultz et al. |
| 2009/0227662 A1 | 9/2009 | Schimmel et al. |
| 2009/0285792 A1 | 11/2009 | Friedlander et al. |
| 2010/0003230 A1 | 1/2010 | Glidden |
| 2010/0028352 A1 | 2/2010 | Greene et al. |
| 2010/0092434 A1 | 4/2010 | Belani et al. |
| 2010/0138941 A1 | 6/2010 | Kim et al. |
| 2010/0297149 A1 | 11/2010 | Zhou et al. |
| 2010/0310576 A1 | 12/2010 | Adams et al. |
| 2011/0110917 A1 | 5/2011 | Schimmel et al. |
| 2011/0117572 A1 | 5/2011 | Kim et al. |
| 2011/0136119 A1 | 6/2011 | Kim et al. |
| 2011/0150885 A1 | 6/2011 | Watkins et al. |
| 2011/0189195 A1 | 8/2011 | Kim et al. |
| 2011/0250701 A1 | 10/2011 | Kim et al. |
| 2011/0256119 A1 | 10/2011 | Kim et al. |
| 2012/0004185 A1 | 1/2012 | Greene |
| 2012/0015383 A1 | 1/2012 | Park et al. |
| 2012/0058133 A1 | 3/2012 | Whitman et al. |
| 2012/0064082 A1 | 3/2012 | Watkins et al. |
| 2013/0224174 A1 | 8/2013 | Greene et al. |
| 2013/0236455 A1 | 9/2013 | Greene et al. |
| 2014/0363415 A1 | 12/2014 | Greene et al. |

FOREIGN PATENT DOCUMENTS

| | | |
|---|---|---|
| CN | 1352242 | 6/2002 |
| CN | 1352252 | 6/2002 |
| EP | 0893494 | 1/1999 |
| EP | 0893496 | 1/1999 |
| EP | 0897004 | 2/1999 |
| EP | 1275720 | 1/2003 |
| EP | 1300468 | 4/2003 |
| EP | 1377305 | 1/2009 |
| EP | 1776138 | 10/2009 |
| EP | 1274834 | 7/2010 |
| WO | WO 97/26351 | 7/1997 |
| WO | WO 97/39017 | 10/1997 |
| WO | WO 99/45130 | 9/1999 |
| WO | WO 01/74841 | 10/2001 |
| WO | WO 01/75078 | 10/2001 |
| WO | WO 01/90330 | 11/2001 |
| WO | WO 01/94568 | 12/2001 |
| WO | WO 02/055663 | 7/2002 |
| WO | WO 02/059323 | 8/2002 |
| WO | WO 02/067970 | 9/2002 |
| WO | WO 03/009813 | 2/2003 |
| WO | WO 03/080648 | 10/2003 |
| WO | WO 03/094862 | 11/2003 |
| WO | WO 2005/102395 | 11/2005 |
| WO | WO 2005/117954 | 12/2005 |
| WO | WO 2006/016217 | 2/2006 |
| WO | WO 2006/057500 | 6/2006 |
| WO | WO 2007/064941 | 6/2007 |
| WO | WO 2008/007818 | 1/2008 |
| WO | WO 2008/016356 | 2/2008 |
| WO | WO 2008/133359 | 11/2008 |
| WO | WO 2009/114623 | 9/2009 |
| WO | WO 2009/152247 | 12/2009 |
| WO | WO 2009/158649 | 12/2009 |
| WO | WO 2010/021415 | 2/2010 |
| WO | WO 2010/041892 | 4/2010 |
| WO | WO 2010/041913 | 4/2010 |
| WO | WO 2010/090471 | 8/2010 |
| WO | WO 2010/096170 | 8/2010 |
| WO | WO 2010/099477 | 9/2010 |
| WO | WO 2010/107825 | 9/2010 |
| WO | WO 2010/120509 | 10/2010 |
| WO | WO 2011/072265 | 6/2011 |
| WO | WO 2011/072266 | 6/2011 |
| WO | WO 2011/097031 | 8/2011 |
| WO | WO 2012/021247 | 2/2012 |

OTHER PUBLICATIONS

International Preliminary Report on Patentability for International Application No. PCT/US2009/046910, dated Dec. 13, 2010.
International Search Report and Written Opinion for International Application No. PCT/US2009/046910, mailed Mar. 4, 2010.
Supplementary European Search Report for European Application No. 06838844.6, mailed Apr. 9, 2009.
Office Action for European Patent Application No. 06838844.6, mailed Apr. 9, 2009.
Office Action for U.S. Appl. No. 12/085,884, mailed Jan. 20, 2011.
International Preliminary Report on Patentability for International Application No. PCT/US2006/046106, dated Jun. 4, 2008.
International Search Report and Written Opinion for International Application No. PCT/US2006/046106, mailed Aug. 9, 2007.
International Preliminary Report on Patentability for International Application No. PCT/US2010/025642, dated Aug. 30, 2011.
International Search Report and Written Opinion for International Application No. PCT/US2010/025642, mailed Oct. 29, 2010.
Office Action for U.S. Appl. No. 12/751,358, mailed Oct. 3, 2011.
Office Action for U.S. Appl. No. 12/751,358, mailed Mar. 3, 2011.
International Preliminary Report on Patentability for International Application No. PCT/US2010/029377, dated Oct. 4, 2011.
International Search Report and Written Opinion for International Application No. PCT/US2010/029377, mailed Jan. 26, 2011.
International Preliminary Report on Patentability for International Application No. PCT/US2010/027525, dated Sep. 20, 2011.
International Search Report and Written Opinion for International Application No. PCT/US2010/027525, mailed Jan. 10, 2011.
International Search Report and Written Opinion for International Application No. PCT/US2010/059964, mailed Aug. 25, 2011.
International Search Report and Written Opinion for International Application No. PCT/US2010/059963, mailed May 12, 2011.
International Search Report and Written Opinion for International Application No. PCT/US2011/000210, mailed Aug. 12, 2011.
International Preliminary Report on Patentability for International Application No. PCT/US2011/043756, dated Jan. 15, 2013.
Adams, M. D. et al., "The genome sequence of drosophila melanogaster," Science, 287(5961):2185-2195 (2000).
Amaar, Y. G. et al., "Cloning and characterization of the C.elegans histidyl-tRNA synthetase gene," Nucleic Acids Research, 21(18):4344-4347 (1993).
Antonellis, A. et al., "Functional Analyses of Glycyl-tRNA Synthetase Mutations Suggest a Key Role for tRNA-Charging Enzymes in Peripheral Axons," The Journal of Neuroscience, 26(41):10397-10406 (2006).
Banks, G. T. et al., "Mutant Glycyl-tRNA Synthetase (Gars) Ameliorates SOD1$^{G93A}$ Motor Neuron Degeneration Phenotype but Has Little Affect on Loa Dynein Heavy Chain Mutant Mice," PLoS One, 4(7):e6218 (2009).
Blumen, S. C. et al., "Mutational analysis of glycyl-tRNA synthetase (GARS) gene in Hirayama Disease," Amyotroph Lateral Scler., 11(1-2):237-239 (2010).
Broun, P. et al., "Catalytic plasticity of fatty acid modification enzymes underlying chemical diversity of plant lipids," Science, 282:1315-1317 (1998).
Brown, M. V. et al., "Mammalian aminoacyl-tRNA synthetases: Cell signaling functions of the protein translation machinery," Vascular Pharmacology, 52(1-2):21-26 (2010).
Cader, M. Z. et al., "Crystal structure of human wildtype and S581L-mutant glycyl-tRNA synthetase, an enzyme underlying distal spinal muscular atrophy," FEBS Letters, 581(16):2959-2964 (2007).
Chica, R. A. et al., "Semi-rational approaches to engineering enzyme activity: combining the benefits of directed evolution and rational design," Curr. Opin. Biotechnol., 16:378-384 (2005).
Delgado, C. et al., "The uses and properties of PEG-linked proteins," Critical Reviews in Therapeutic Drug Carrier Systems, 9(3,4):249-304 (1992).

(56) References Cited

OTHER PUBLICATIONS

Devos, D. et al., "Practical limits of function prediction," Proteins: Structure, Function, and Genetics, 41:98-107 (2000).
EBI Accession No. GSP: ARB30818, "Cotton protein for improving plant biological properties, 100753," retrieved Oct. 20, 2009.
Ewalt, K. L. et al., "Activation of Angiogenic Signaling Pathways by Two Human tRNA Synthetases," Biochemistry, 41(45):13344-13349 (2002).
Frommhold, D. et al., "Sialyltransferase ST3Gal-IV controls CXCR2-mediated firm leukocyte arrest during inflammation," Journal of Experimental Medicine, 205(6):1435-1446 (2008).
Garcia-Lozano, J. R. et al., "Detection of anti-PL-12 autoantibodies by ELISA using a recombinant antigen; study of the immunoreactive region," Clin. Exp. Immunol., 114:161-165 (1998).
GenBank Accession No. AK074524, Mar. 25, 2002.
GenBank Accession No. AU126197, Oct. 23, 2000.
GenBank Accession No. AW976267, Jun. 2, 2000.
GenBank Accession No. BI258770, Jul. 16, 2001.
GenBank Accession No. BP423196, May 27, 2005.
GenBank Accession No. CA314607, Nov. 4, 2002.
GenBank Accession No. DA018291, Nov. 2, 2005.
GenBank Accession No. DA386636, Nov. 5, 2005.
GenBank Accession No. DA478765, Nov. 6, 2005.
GenBank Accession No. DA552410, Nov. 5, 2005.
GenBank Accession No. DA576766, Nov. 5, 2005.
GenBank Accession No. DB488998, Mar. 31, 2006.
GenBank Accession No. DC366890, Apr. 27, 2007.
GenBank Accession No. DB058369, Dec. 10, 2005.
GenBank Accession No. AA174042, Sep. 30, 1997.
GenBank Accession No. A1963202, Aug. 20, 1999.
GenBank Accession No. CR594947, "full-length cDNA clone CS0DE014YC03 of Placenta of *Homo sapiens* (human)," retrieved from http://www.ncbi.nlm.nih.gov/nuccore/50475754, Mar. 25, 2010.
GenBank Accession No. Q7QD89, Anopheles gambiae Sequence Committee, submitted Apr. 2002, [Retrieved from the Internet Apr. 24, 2007], <URL: http://www.ncbi.nlm.nih.gov/entrez/viewer.fcgi?db=protein&val=74803944>.
GenBank Accession No. Q9W60, published May 1, 2000.
GenBank Accession No. U09510, "Human glycyl-tRNA synthetase mRNA, complete cds," retrieved from http://www.ncbi.nlm.nih.gov/nuccore/595304, Apr. 1, 2010.
GenBank Accession No. U09587, Human glycyl-tRNA synthetase mRNA, complete cds, Dec. 9, 1994.
Goldgur, Y. et al., "The crystal structure of phenylalanyl-tRNA synthetase from Thermus thermophilus complexed with cognate tRNA," Structure, 5:59-68 (1997).
Greenberg, Y. et al., "The novel fragment of tyrosyl tRNA synthetase, mini-TyrRS, is secreted to induce an angiogenic response in endothelial cells," FASEB Journal, 22(5):1597-1605 (2008).
Guijarro, J. I. et al., "Structure and Dynamics of the Anticodon Arm Binding Domain of Bacillus stearothermophilus Tyrosyl-tRNA Synthetase," Structure, 10:311-317 (2002).
Guo, R-T. et al., "Crystal structures and biochemical analyses suggest a unique mechanism and role for human glycyl-tRNA synthetase in Ap4A homeostasis," Journal of Biological Chemistry, 284(42):28968-28976 (2009).
Guo, M. et al., "Functional expansion of human tRNA synthetases achieved by structural inventions," FEBS Letters, 584(2):434-442 (2010).
Guo, M. et al., "New functions of aminoacyl-tRNA synthetases beyond translation," Nature Reviews Molecular Cell Biology, 11:668-674 (2010).
Hausmann, C. D. et al., "Aminoacyl-tRNA synthetase complexes: molecular multitasking revealed," FEMS Microbiol. Rev., 32(4):705-721 (2008).
Hou, Y-M. et al., "Sequence determination and modeling of structural motifs for the smallest monomeric aminoacyl-tRNA synthetase," Proc. Nat. Acad. Sci., 88(3):976-980 (1991).

Ivakhno, S. S. et al., "Cytokine-Like Activities of Some Aminoacyl-tRNA Synthetases and Auxiliary p43 Cofactor of Aminoacylation Reaction and Their Role in Oncogenesis," Exp. Oncol., 26(4):250-255 (2004).
Jacobo-Molina, A. et al., "cDNA Sequence, Predicted Primary Structure, and Evolving Amphiphilic Helix of Human Aspartyl-tRNA Synthetase," Journal of Biological Chemistry, 264(28):16608-16612 (1989).
Jordanova, A. et al., "Disrupted function and axonal distribution of mutant tyrosyl-tRNA synthetase in dominant intermediate Charcot-Marie-Tooth neuropathy," Nature Genetics, 38(2):197-202 (2006).
Jura, M. et al., "Comprehensive Insight into Human Aminoacyl-tRNA Synthetases as Autoantigens in Idiopathic Inflammatory Myopathies," Critical Reviews in Immunology, 27(6):559-572 (2007).
Kapoor, M. et al., "Mutational separation of aminoacylation and cytokine activities of human tyrosyl-tRNA synthetase," Chemistry & Biology, 16(5):531-539 (2009).
Kimchi-Sarfaty, C. et al., "A 'Silent' polymorphism in the MDR1 gene changes substrate specificty," Science, 315:525-528 (2007).
Kise, Y. et al., "A short peptide insertion crucial for angiostatic activity of human tryptophanyl-tRNA synthetase," Nature Structural & Molecular Biology, 11(2):149-156 (2004).
Kochendoerfer, G. G., "Site-specific polymer modification of therapeutic proteins," Current Opinion in Chemical Biology, 9:555-560 (2005).
Kovaleski, B. J. et al.,"In vitro characterization of the interaction between HIV-1 Gag and human lysyl-tRNA synthetase," J. Bio. Chem., 281(28):19449-19456 (2006).
Levine, S. M. et al., "Anti-aminoacyl tRNA synthetase immune responses: insights into the pathogenesis of the idiopathic inflammatory myopathies," Current Opinion in Rheumatology, 15(6):708-713 (2003).
Link, A. J. et al., "Discovery of aminoacyl-tRNA synthetase activity through cell-surface display of noncanonical amino acids," Proc. Nat. Acad. Sci., 103(27):10180-10185 (2006).
Molecular Modeling Database (MMDB), "Solution Structures of the Whep-trs domain of human histidyl-trna synthetase," MMDB ID No. 35920, available for www.ncbi.nlm.nih.gov/Structure/mmdb, accessed Aug. 24, 2012.
Motley et al., "Charcot-Marie-Tooth-Linked Mutant GARS is Toxic to Peripheral Neurons Independent of Wild-Type GARS Levels," PLoS Genetics, 7(12):e1002399 (2011).
Motley, W. W. et al., "GARS axonopathy: not every neuron's cup of tRNA," Trends Neurosci., 33(2):59 (2010).
Nackley, A. G. et al., "Human Caechol-O-Methyltransferase haplotypes modulate protein expression by altering mRNA secondary structure," Science, 314:1930-1933 (2006).
Nangle, L. A. et al., "Charcot-Marie-Tooth disease-associated mutant tRNA synthetases linked to altered dimer interface and neurite distribution defect," PNAS, 104(27):11239-11244 (2007).
Ngo, J. T. et al., "Computational complexity, protein structure prediction, and the Levinthal paradox," In the Protein Folding Problem and Tertiary Structure Prediction, Merz et al. (ed.), Birkhauser, Boston, MA, pp. 433 and 492-495 (1994).
Nichols, R. C. et al., "Human isoleucyl-tRNA synthetase: sequence of the cDNA, alternative mRNA splicing, and the characteristics of an unusually long C-terminal extension," Gene, 155(2):299-304 (1995).
Park, S. G., et al., "Aminoacyl tRNA synthetases and their connections to disease," PNAS, 105(32):11043-11049 (2008).
Park, S. G. et al., "Dose-dependent biphasic activity of tRNA synthetase-associating factor, p43, in angiogenesis," The Journal of Biological Chemistry, 277(47):45243-45248 (2002).
Park, S. G. et al., "Is there an answer? Do aminoacyl-tRNA synthetases have biological functions other than in protein biosynthesis?" IUBMB Life, 58(9):556-558 (2006).
Park, M. C. et al., "Secreted human glycyl-tRNA synthetase implicated in defense against ERK-activated tumorigenesis," Proc. Natl. Acad. Sci. USA [online], Retrieved from the Internet: <URL:http://www.pnas.org/cgi/doi/10.1073/pnas.1200194109>, Published on Feb. 15, 2012.

(56) References Cited

OTHER PUBLICATIONS

Protein Purification—Handbook, Amersham Parmacia Biotech AB (1999).
Quesniaux, V. F.J. et al., "Hematopoiesis, including lymphocyte developmet and maturation," Principles of Immunopharmacology, pp. 3-17 (2005).
Reed, V. S. et al., "Characterization of a Novel N-terminal Peptide in Human Aspartyl-tRNA Synthetase," Journal of Biological Chemistry, 269(52):32937-32941 (1994).
Richardson, R. M. et al., "Role of the cytoplasmic tails of CXCR1 and CXCR2 in mediating leukocyte migration, activation, and regulation," Journal of Immunology, 170(6):2904-2911 (2003).
Sauna, Z. E. et al., "Silent polymorhisms speak: How they affect pharmacogenomics and the treatment of cancer," Cancer Res., 67(20):9609-9612 (2007).
Seburn, K. L. et al., "An active dominant mutation of glycyl-tRNA synthetase causes neuropathy in a Charcot-Marie-Tooth 2D mouse model," Neuron, 51(6):715-726 (2006).
Sen, S. et al., "Developments in directed evolution for improving enzyme functions," Appl. Biochem. Biotechnol., 143:212-223 (2007).
Smith, D. F. et al., "Leukocyte phosphoinositide-3 kinase γ is required for chemokine-induced, sustained adhesion under flow in vivo," Journal of Leukocyte Biology, 80(6):1491-1499 (2006).
Storkebaum, E. et al., "Dominant mutations in the tyrosyl-tRNA synthetase gene recapitulate in Drosophila features of human Charcot-Marie-Tooth neuropathy," PNAS, 106(28):11782-11787 (2009).
Targoff, I. N. et al., "Antibodies to glycyl-transfer RNA synthetase in patients with myositis and interstitial lung disease," Arthritis Rheum., 35(7):821-830 (1992).
Traves, S. L. et al., "Specific CXC but not CC chemokines cause elevated monocyte migration in COPD: a role for $CXCR_2$," Journal of Leukocyte Biology, 76(2):441-450 (2004).
Veronese, F. M. et al., "Preface: Introduction and overview of peptide and protein pegylation," Advanced Drug Delivery Reviews, 54:453-456 (2002).
Wakasugi, K. et al., "Two distinct cytokines released from a human aminoacyl-tRNA synthetase," Science, 284:147-151 (1999).
Wakasugi, K. et al., "A human aminoacyl-tRNA synthetase as a regulator of angiogenesis," Proc. Natl. Acad. Sci., 99(1):173-177 (2002).
Wakasugi, K. et al., "Induction of angiogenesis by a frament of human tyrosyl-tRNA synthetase," The Journal of Biological Chemistry, 277(23):20124-20126 (2002).
Wasenius, V-M et al., "Hepatocyte Growth Factor Receptor, Matrix Metalloproteinase-11, Tissue Inhibitor of Metalloproteinase-1, and Fibronectin Are Up-Regulated in Papillary Thyroid Carcinoma: A cDNA and Tissue Microarray Study," Clin. Cancer Res., 9:68-75 (2003).
Whisstock, J. C. et al., "Prediction of protein function from protein sequence," Q. Rev. Biophysics., 36(3):307-340 (2003).
Williams, J. et al., "Cloning, sequencing and bacterial expression of human glycine tRNA synthetase," Nucleic Acids Res., 23(8):1307-1310 (1995).
Wishart, M. J. et al., "A single mutation converts a novel phosphotyrosine binding domain into a dual-specificity phosphatase," J. Biol. Chem., 270(45):26782-26785 (1995).
Witkowski, A. et al., "Conversion of β-ketoacyl synthase to a Malonyl Decarboxylase by replacement of the active cysteine with glutamine," Biochemistry, 38:11643-11650 (1999).
Xie et al., "Crystallization and preliminary X-ray analysis of a native human tRNA synthetase whose allelic variants are associated with Charcot-Marie-Tooth disease," Acta. Cryst., F62:1243-1246 (2006).
Xie, W. et al., "Long-range structural effects of a Charcot-Marie-Tooth disease-causing mutation in human glycyl-tRNA synthetase," PNAS, 104(24):9976-9981 (2007).
Yang, X-L et al., "Crystal structure of a human aminoacyl-tRNA synthetase cytokine," PNAS, 99(24):15369-15374 (2002).
Yang, X-L et al., "Relationship of two human tRNA synthetases used in cell signaling," Trends in Biochemical Sciences, 29(5):250-256 (2004).
Yang, X-L et al., "Crystal structures that suggest late development of genetic code components for differentiating aromatic side chains," PNAS, 100(26):15376-15380 (2003).
Yang, X-L et al., "Gain-of-Function Mutational Activation of Human tRNA Synthetase Procytokine," Chemistry & Biology, 14(12):1323-1333 (2007).
Yu, Y. et al., "Crystal structure of human tryptophanyl-tRNA synthetase catalytic fragment," The Journal of Biological Chemistry, 279(9):8378-8388 (2004).
Zalipsky, S. et al., "Use of functionalized poly(ethylene glycol)s for modification of polypeptides," Polyethylene glycol chemistry: Biotechnical and Biomedical Applications, pp. 347-370, Plenum Press, New York (1992).
Zhou, Q. et al., "Orthogonal use of a human tRNA synthetase active site to achieve multifunctionality," Nature Structural & Molecular Biology, 17(1):57-62 (2010).
Zwijnenburg, P. J. G. et al., B-1426, "Tyrosyl tRNA synthetase is a chemotactic factor in cerebrospinal fluid from patients with bacterial meningitis," Abstracts of the 42nd Interscience Conference on Antimicrobial Agents and Chemotherapy, San Diego, California, Sep. 27-30, 2002, Session 156(B), p. 55.
Database Geneseq [Online], Jul. 10, 2008, "Cotton protein for improving plant biological properties, 100743," XP002551288, retrieved from EBI accession No. GSP:ARB30808, Database accession No. ARB30808.

* cited by examiner

Figure 1. Human glycyl-tRNA synthetase protein
(A) Domain structure, (B) sequence, (C) SDS-PAGE gel (D) Digestion with PMN Elastase

```
1 MDGAGAEEVLAPLRLAVRQGGDLVRKLKEDKAPQVD
  VDKAVAELKARKRVLEAKELALQPKDDVDRAKMEDTL
  KRRFFYDQAFAIYGGVSGLYDFGPVGCALKNNIIQTWR
  QHFIQEQILEIDCTMLTPEPVLKTSGHVDKFADFMVK
  DVKNGECFRADHLLKAHLQKLMSDKKCSVEKSEMES
  VLAQLDNYGQELADLFVNYNVKSPITGNDLSPPVSFN
  LMFKTFIGPGGNMPGYLRPETAQGIFLNFKRLLEFNQG
  KLPFAAAQIGNSFRNEISPRSGLRVREFTMAEIEHPVD
  PSEKDHPKFQNVADLHLYLYSAKAQVSGQSARKMRLG
  DAVEQGVINNTVLGYFIGRIYLYLTKVGISPDKLRFRQH
  MENEMAHYACDCWDAESKTSYGMIEVGCADRSCYD
  LSCHARATKYPLVAEKPLKEPKTVNVQFEPSKGAIGK
  AYKKDAKLVMEYLAICDECYITEMEMLLNEKGEFTIETE
  GKTFQLTKDMINVKRFQKTLYEEVVPNMEPSFGLGRI
  MYTVFEHTFHYREGDEQRTFFSFPAVVAPFKCSVLPL
  SQNQEFMPFVKELSEALTRHGVSHKVDDSSGBIGRRY
  ARTDEIGVAFGVTIDFDTVNKTPHTATLRDRDSMRQIR
  AEISELPSIVQDLANGNITWADVEARYPLFEGQETGKK
  ETIEE888
```

*FIG. 1B*

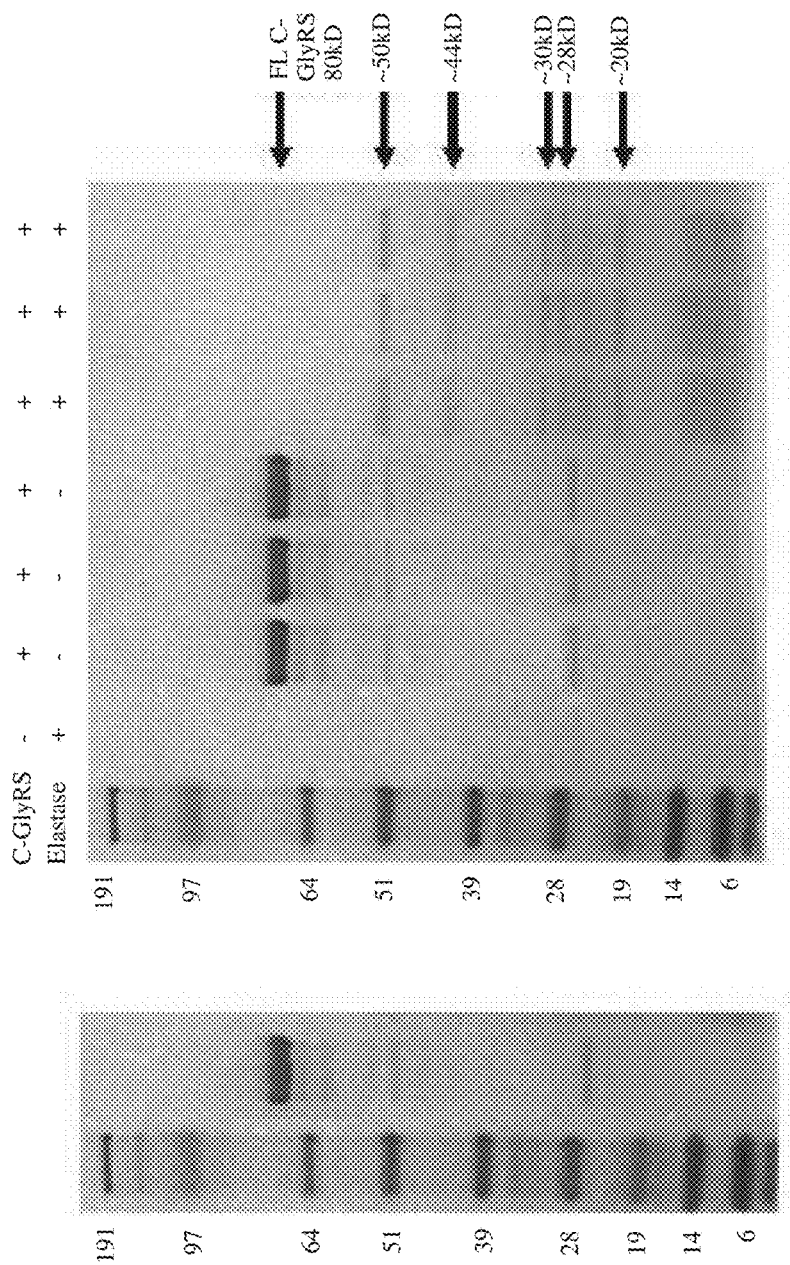

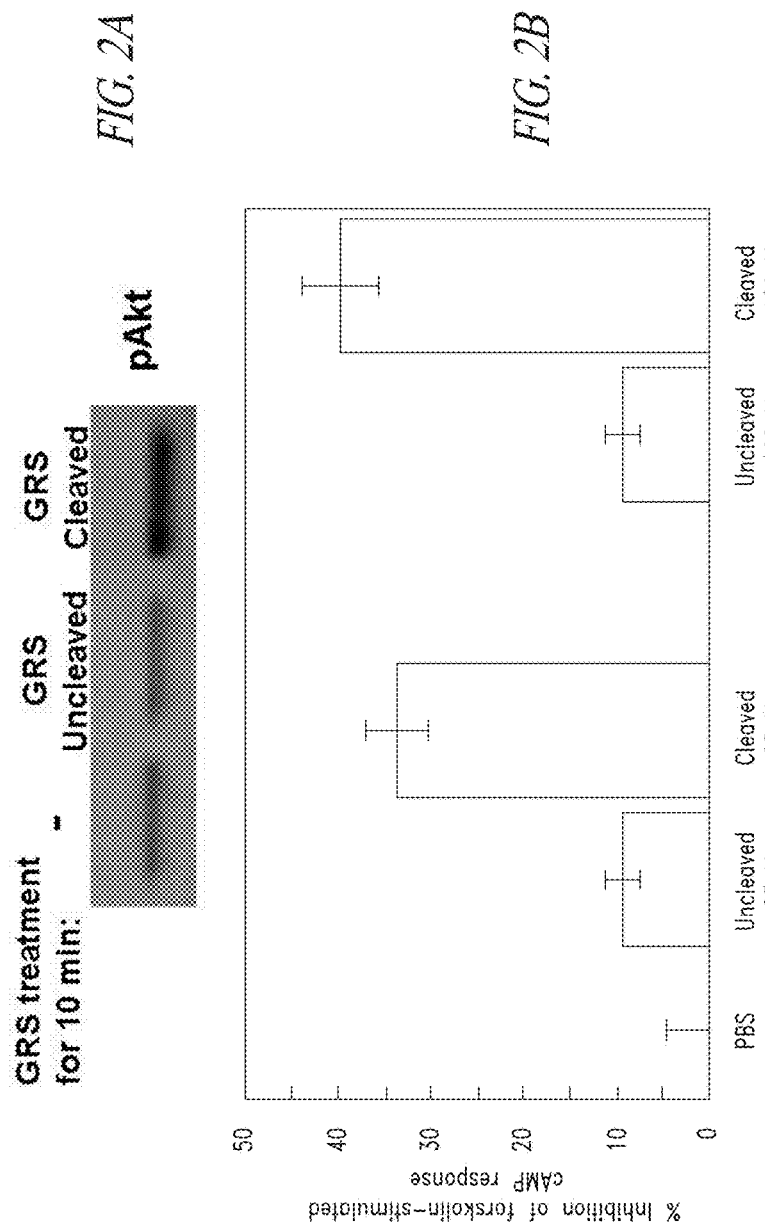

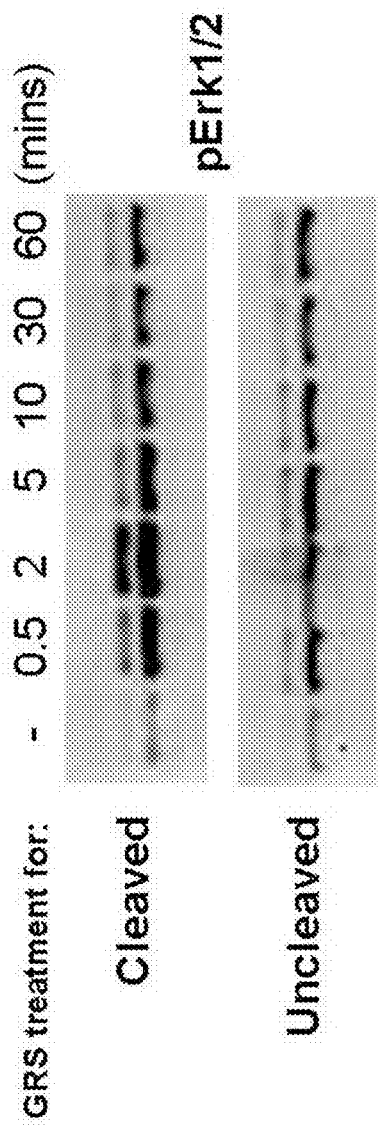
Figure 3. Cleaved GRS fragments induce signaling in THP-1 monocytes
(A) Time-course of activation of Erk1/2

Mass spectrometric identification of GRS fragment boundaries (A) Protease cleavage sites were determined by LC/MS/MS (B) Structure of GRS fragment, termed G6, within the context of full length glycyl-tRNA synthetase dimer Supernatant band 9: GRS (fragment) MW:~45-50 kd
Spectral counts: 19 (peptides covered are in bold)
MDGAGAEEVLAPLRLAVRQ
QGDLVRKLKEDKAPQVDVDKAVAELKARKRVLEAKELALQPKDDIVDRAKMEDTLKRRFF
YDQAFAIYGGVSGLYDFGPVGCALKNNIIQTWRQHFIQEEQILEIDCTMLTPEPVLKTSG
HVDKFADFMVKDVKNGECFRADHLLKAHLQKLMSDKKCSVEKKSEMESVLAQLDNYGQQE
LADLFVNYNVKSPITGNDLSPPVSFNLMFKTFIGPGGNMPGYLRPETAQGIFLNFKRLLE
FNQGKLPFAAAQIGNSFRNEISPRSGLIRVREFTMAEIEHFVDPSEKDHPKFQNVADLHL
YLYSAKAQVSGQSARKMRLGDAVEQGVINNTVLGYFIGRIYLYLTKVGISPDKLRFRQHM
ENEMAHYACDCWDAESKTSYGWIEIVGCADRSCYDLSCHARATKVPLVAEKPLKEPKTVN
VVQFEPSKGAIGKAYKKDAKLVMEYLAICDECYITEMEMLLNEKGEFTIETEGKTFQLTK
DMINVKRFQKTLYVEEVVPNVIEPSFGLGRIMYTVFEHTFHVREGDEQRTFFSFPAVVAP
FKCSVLPLSQNQEFMPFVKELSEALTRHGVSHKVDDSSGSIGRRYARTDEIGVAFGVTID
FDTVNKTPHTATLRDRDSMRQIRAEISELPSIVQDLANGNITWADVEARYPLFEGQETGK
KETIEE

*FIG. 16A*

Supernatant band 18: GRS (fragment) MW:~15 kd
Spectral counts: 3, (peptides covered are in bold)

MDGAGAEEVLAPLRLAVRQ
QGDLVRKLKEDKAPQVDVDKAVAELKARKRVLEAKELALQPKDDIVDRAKMEDTLKRRFF
YDQAFAIYGGVSGLYDFGPVGCALKNNIIQTWRQHFIQEEQILEIDCTMLTPEPVLKTSG
HVDKFADFMVKDVKNGECFRADHLLKAHLQKLMSDKKCSVEKKSEMESVLAQLDNYGQQE
LADLFVNYNVKSPITGNDLSPPVSFNLMFKTFIGPGGNMPGYLRPETAQGIFLNFKRLLE
FNQGKLPFAAAQIGNSFRNEISPRSGLIRVREFTMAEIEHFVDPSEKDHPKFQNVADLHL
YLYSAKAQVSGQSARKMRLGDAVEQGVINNTVLGYFIGRIYLYLTKVGISPDKLRFRQHM
ENEMAHYACDCWDAESKTSYGWIEIVGCADRSCYDLSCHARATKVPLVAEKPLKEPKTVN
VVQFEPSKGAIGKAYKKDAKLVMEYLAICDECYITEMEMLLNEKGEFTIETEGKTFQLTK
DMINVKRFQKTLYVEEVVPNVIEPSFGLGRIMYTVFEHTFHVREGDEQRTFFSFPAVVAP
FKCSVLPLSQNQEFMPFVKELSEALTRHGVSHKVDDSSGSIGRRYARTDEIGVAFGVTID
FDTVNKTPHTATLRDRDSMRQIRAEISELPSIVQDLANGNITWADVEARYPLFEGQETGK
KETIEE

*FIG. 16B*

COMPOSITIONS AND METHODS COMPRISING GLYCYL-TRNA SYNTHETASES HAVING NON-CANONICAL BIOLOGICAL ACTIVITIES

CROSS-REFERENCE TO RELATED APPLICATIONS

This application is a Continuation of U.S. application Ser. No. 14/262,247, filed Apr. 25, 2014; which is a Continuation of U.S. application Ser. No. 13/753,272, filed Jan. 29, 2013, now U.S. Pat. No. 8,747,840, issued Jun. 10, 2014; which is a Continuation of Ser. No. 12/492,925, filed Jun. 26, 2009, now U.S. Pat. No. 8,404,471, issued Mar. 26, 2013; which claims the benefit under 35 U.S.C. §119(e) of U.S. Provisional Patent Application No. 61/095,548 filed Sep. 9, 2008; and U.S. Provisional Patent Application No. 61/076,098 filed Jun. 26, 2008, which are incorporated by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ATYR-008_05US_ST25.txt. The text file is about 23 KB, was created on Sep. 3, 2015 and is being submitted electronically via EFS-Web, concurrent with the filing of the specification.

BACKGROUND OF THE INVENTION

Field of the Invention

The present invention relates generally to glycyl-tRNA synthetase (GlyRS) polypeptides, compositions comprising such polypeptides, and methods of using same.

Description of the Related Art

Aminoacyl-tRNA synthetases, which catalyze the aminoacylation of tRNA molecules, are essential for decoding genetic information during the process of translation. Each of the eukaryotic tRNA synthetases consists of a core enzyme, which is closely related to the prokaryotic counterpart of the tRNA synthetase, and an additional domain that is appended to the amino-terminal or carboxyl-terminal end of the core enzyme. Human tyrosyl-tRNA synthetase (TyrRS), for example, has a carboxyl-terminal domain that is not part of prokaryotic and lower eukaryotic TyrRS molecules.

Several aminoacyl-tRNA synthetases have been demonstrated to have non-canonical functions distinct from their involvement in translation. For example, mini-tyrosyl tRNA synthetase (mini-TyrRS), the N-terminal domain of TyrRS which corresponds to amino acid residues 1-364 and is cleaved by polymorphonuclear cell elastase and plasmin, exhibits non-canonical biologies not found in the full-length protein. In vitro, mini-TyrRS has been shown to stimulate neutrophil activation and chemotaxis, endothelial cell proliferation and migration, and is pro-angiogenic in chick chorioallantoic membrane (CAM) and mouse matrigel assays. Mini-TyrRS has an ELR motif that, like CXC-chemokines such as IL-8, is involved in many of its chemokine and angiogenic activities. As in other ELR-containing cytokines, mutation of this motif inhibits mini-TyrRS binding to and stimulation of leukocytes and angiogenesis.

In addition, truncated forms of TrpRS have been demonstrated to have anti-angiogenic properties. In normal human cells, there are two forms of TrpRS that can be detected: a major form consisting of the full-length molecule (amino acid residues 1-471) and a minor truncated form. The minor form is generated by the deletion of an amino-terminal domain through alternative splicing of the pre-mRNA and is termed mini-TrpRS. The amino-terminus of miniTrpRS has been determined to be the methionine residue at position 48 of the full-length TrpRS molecule. Alternatively, truncated TrpRS can be generated by proteolysis. For example, bovine TrpRS is highly expressed in the pancreas and is secreted into the pancreatic juice, thus resulting in the production of a truncated TrpRS molecule. Additional studies indicate that mini-TrpRS inhibits VEGF-induced cell proliferation and migration (Wakasugi et al., Proc. Natl. Acad. Sci. 99: 173-177 (2002)). In particular, a chick CAM assay shows that mini TrpRS blocks angiogenic activity of VEGF. In contrast, the full-length TrpRS does not inhibit angiogenesis. Thus, removal of the first 48 amino acid residues exposes the anti-angiogenic activity of TrpRS. Therefore, as with TyrRS, certain forms of TrpRS possess activities other than the aminoacylation of tRNA.

Given these observations of non-canonical and therapeutically relevant activities associated with alternative forms of TyrRS and TrpRS, there is a need to identify biologically relevant forms of other aminoacyl-tRNA synthetase proteins in order to exploit the full therapeutic potential of this family of proteins. Accordingly, the present invention addresses these needs and offers other related advantages.

SUMMARY OF THE INVENTION

The present invention stems from the discovery that glycyl-tRNA synthetase (GlyRS) and certain polypeptides derived from GlyRS possess non-canonical biological activities of therapeutic relevance. Therefore, according to one aspect, the present invention provides isolated GlyRS polypeptides having at least one non-canonical biological activity, as well as active fragments and variants thereof which substantially retain said non-canonical activity. "Non-canonical" activity," as used herein, refers generally to an activity possessed by a GlyRS polypeptide of the invention that is other than the addition of glycine onto a tRNA$^{Gly}$ molecule. As detailed herein, in certain embodiments, a non-canonical biological activity exhibited by a GlyRS polypeptide of the invention may include, but is not limited to, modulation of cell proliferation, modulation of apoptosis, modulation of cell migration, modulation of cell signaling and/or modulation of cytokine production and/or secretion. In more specific embodiments, the activity includes modulation of Akt-mediated cell signaling, modulation of Erk1/2-mediated cell signaling and modulation of GPCR-mediated cell signaling, modulation of endothelial cell tube formation, and modulation of cell binding. In other specific embodiments, the activity includes modulation of CD71 and/or CD80. In yet other specific embodiments, the activity includes modulation of cytokine production and/or release, wherein the cytokine is selected from the group consisting of TNF-α, IL1-β, IL-6, IL-8, IL-10, IL-12p40, MIP1-α, MIP-1β, GRO-α, MCP-1 and IL-1ra.

In certain embodiments, the GlyRS polypeptide of the invention is a contiguous fragment of a full length mammalian GlyRS protein. In a more specific embodiment, the GlyRS polypeptide is a contiguous fragment of the human GlyRS protein sequence set forth in SEQ ID NO: 1. Illustratively, the fragments may be of essentially any length, and further provided they retain at least one non-canonical biological activity of interest. In certain illustrative embodiments, a GlyRS polypeptide of the invention will range in size from about 50-100, 50-200, 50-300, 50-400, 50-500 or 50-600 amino acids in length. In other embodiments, the GlyRS polypeptide of the invention will range in size from about 100-200, 100-300, 100-400, 100-500 or 100-600 amino acids in length. In still other illustrative embodiments, the GlyRS polypeptide of the invention will range in size from about 200-300, 200-400, 200-500 or 200-600 amino acids in length.

In further embodiments of the invention, a GlyRS polypeptide comprises an active variant (i.e., retains at least one non-canonical biological activity of interest) of a fragment of a GlyRS protein sequence, such as the human GlyRS protein sequence set forth in SEQ ID NO: 1. In a more specific embodiment, the active variant is a polypeptide having at least 70%, 80%, 90%, 95% or 99% identity along its length to a human glycyl-tRNA synthetase sequence set forth in SEQ ID NO: 1.

Other embodiments of the invention provide GlyRS splice variants and mutants, whether naturally or non-naturally occurring, that possess one or more non-canonical activities as described herein.

In more specific embodiments of the invention, a GlyRS polypeptide comprises a fragment of a GlyRS sequence (e.g., SEQ ID NO: 1), consisting essentially of amino acid residues 57-685, 214-685, 239-685, 311-685, 439-685, 511-658, 214-438, 367-438, 214-420, 214-338, 85-127 or 25-56, 1-213, 1-61, 85-214, 333-685, 128-685, 265-685 or 483-685, or an active fragment or variant thereof that substantially retains at least one non-canonical biological activity of interest.

In other specific embodiments, the GlyRS polypeptide is not a polypeptide as set forth in any one of NCBI #CR594947, U09587 and/or U09510.

According to another aspect of the invention, there are provided fusion proteins comprising at least one GlyRS polypeptide as described herein and a heterologous fusion partner.

According to another aspect of the invention, there are provided isolated polynucleotides encoding the polypeptides and fusion proteins as described herein, as well as expression vectors comprising such polynucleotides, and host cell comprising such expression vectors.

According to yet another aspect of the invention, there are provided compositions, e.g., pharmaceutical compositions, comprising physiologically acceptable carriers and at least one of the isolated polypeptides, fusion proteins, antibodies, isolated polynucleotides, expression vectors, host cells, etc., of the invention, as described herein.

Also provided by the present invention, in other aspects, are methods for modulating a cellular activity by contacting a cell or tissue with a composition of the invention, as described herein, wherein the cellular activity to be modulated is selected from the group consisting of cell proliferation, modulation of apoptosis, modulation of cell migration, modulation of cell signaling and/or modulation of cytokine production and/or secretion. In more specific embodiments, the cellular activity is selected from the group consisting of modulation of Akt-mediated cell signaling, modulation of Erk1/2-mediated cell signaling, modulation of GPCR-mediated cell signaling, modulation of endothelial cell tube formation, and modulation of cell binding. In other specific embodiments, the cellular activity is selected from the group consisting of modulation of CD71 and/or CD80. In yet other specific embodiments, the cellular activity is selected from the group consisting of modulation of cytokine production and/or release, for example, wherein the cytokine is selected from the group consisting of TNF-α, IL1-β, IL-6, IL-8, IL-10, IL-12p40, MIP1-α, MIP-1β, GRO-α, MCP-1 and IL-1ra.

In other aspects, the present invention provides methods for treating a disease, disorder or other condition in a subject in need thereof by administering a composition according to the present invention. By way of illustration, such diseases, disorders or conditions may include, but are not limited to, cancer, inflammatory disease, immune disease (including autoimmune disease), diseases associated with abnormal hematopoietic activity, diseases where neurogenesis or neuroprotection is desired, metabolic disorders and/or conditions associated with abnormal angiogenesis.

In still other aspects, the polynucleotides, polypeptides, antibodies and/or other compositions of the present invention may be used in essentially any type of screening assay known and available in the art. For example, compositions of the invention (e.g., polypeptides, polynucleotides and/or antibodies) may be used in conjunction with known screening methodologies in order to identify suitable cell types and/or disease conditions amenable to treatment according to the present invention. In other examples, compositions of the invention (e.g., polypeptides, polynucleotides and/or antibodies) may be used in conjunction with known screening methodologies in order to identify agonists, antagonists, binding partners, competitive inhibitors, cellular effectors, and the like, that mediate or modulate, either directly or indirectly, the non-canonical activities of the compositions herein. For example, in a particular embodiment, a screening method is provided for identifying test compounds as inhibitors, or alternatively, potentiators, of a non-canonical activity or of an interaction between a composition of the invention and one or more of its binding partners, cellular effectors and/or cell types subject to modulation. This may include, for example, steps of forming a reaction mixture including: (i) a composition of the invention, (ii) a binding partner, cellular effector and/or cell type known to be bound and/or modulated by said composition, and (iii) a test compound; and detecting whether binding and/or modulation in the presence of the test compound in increased or decreased. A statistically significant change (potentiation or inhibition) in activity or modulation in the presence of the test compound, relative to the effect in the absence of the test compound, indicates a potential agonist (mimetic or potentiator) or antagonist (inhibitor) of binding and/or activity.

BRIEF DESCRIPTION OF SEQUENCE IDENTIFIERS

SEQ ID NO: 1 is the full length amino acid sequence of human cytoplasmic glycyl-tRNA synthetase (GlyRS).

SEQ ID NO: 2 is a nucleic acid sequence encoding the GlyRS polypeptide of SEQ ID NO: 1.

SEQ ID NOs: 3-9 represent illustrative peptide sequences analyzed in determining GlyRS fragment boundaries (see Example 4 & Table 1)

SEQ ID NOs: 10 and 11 are GlyRS sequences used in identifying fragments secreted from LPS-treated mouse macrophage cells (see Example 12 & FIG. 16)

BRIEF DESCRIPTION OF THE DRAWINGS

FIGS. 1A-1D show the domain structure and amino acid sequence of the GlyRS protein (FIG. 1B; SEQ ID NO: 1), and illustrate the SDS-PAGE separation of fragments of GlyRS generated by controlled proteolysis of the full-length GlyRS protein with human neutrophil elastase.

FIGS. 2A-2B demonstrate the activation of Akt and Gi-GPCRs, respectively, in endothelial cells treated with GlyRS fragments of the invention.

FIG. 3 demonstrates the activation of Erk1/2 (mitogen-activated protein kinase Erk1 and Erk2) in monocyte cells treated with GlyRS fragments of the invention.

FIG. 6 (inset) demonstrates that GlyRS fragment G6 signals through select chemokine receptors.

FIG. 16A (SEQ ID NO:1) shows sequence information for supernatant band 9, a GRS fragment having a molecular weight of ~45-50 kd, with relevant peptide sequences shown in bold.

FIG. 16B (SEQ ID NO:1) shows sequence information for supernatant band 18, a GRS fragment having a molecular weight of ~15 kd, with relevant peptide sequences shown in bold.

DETAILED DESCRIPTION OF THE INVENTION

Figure 1A:
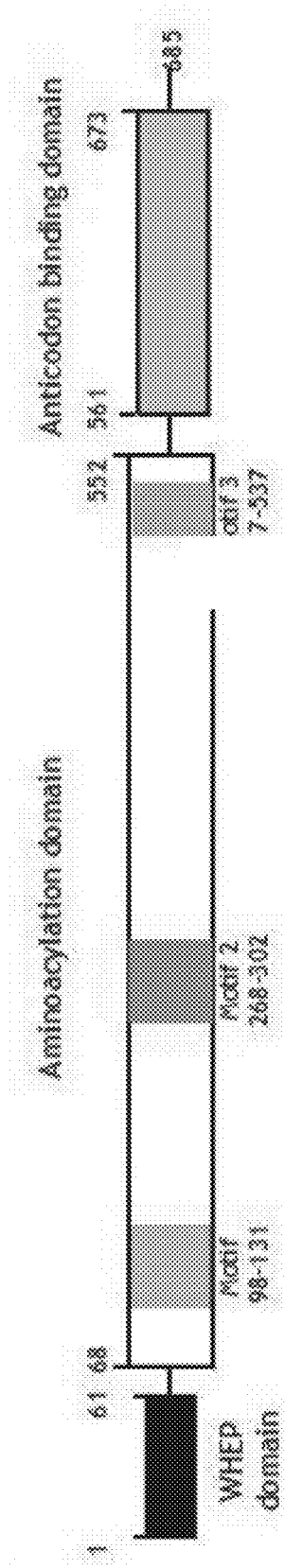

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (2nd Edition, 1989); Maniatis et al., *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); *A Practical Guide to Molecular Cloning* (B. Perbal, ed., 1984).

All publications, patents and patent applications cited herein are hereby incorporated by reference in their entirety.

As used in this specification and the appended claims, the singular forms "a," "an" and "the" include plural references unless the content clearly dictates otherwise.

As used herein, the terms "polypeptide" and "protein" are used according to conventional meaning, i.e., as a sequence of amino acids. Polypeptides are not limited to a specific length, but, in the context of the present invention, typically represent a fragment of a full length protein, and may include post-translational modifications, for example, glycosylations, acetylations, phosphorylations and the like, as well as other modifications known in the art, both naturally occurring and non-naturally occurring. Polypeptides and proteins of the invention may be prepared using any of a variety of well known recombinant and/or synthetic techniques, illustrative examples of which are further discussed below.

Glycyl-tRNA Synthetase Polypeptides

The present invention relates generally to isolated GlyRS polypeptides, polynucleotides encoding such polypeptides, binding agents that bind such polypeptides, analogs, variants and fragments of such polypeptides, etc., as well as compositions and methods of using any of the foregoing.

Therefore, according to one aspect of the invention, there are provided GlyRS polypeptides having non-canonical activities of therapeutic relevance, as well as compositions comprising same. In certain embodiments, the GlyRS polypeptide is a truncated form of a GlyRS protein. A "truncated" GlyRS, as used herein, refers to a glycyl-tRNA synthetase protein which is shorter than its corresponding full length GlyRS protein, for example, due to removal of amino acids from its N- and/or C-terminal ends. The extent of the truncation, that is, the number of N- and/or C-terminal amino acid residues removed from a full length GlyRS protein can vary considerably while still providing desired cellular effects when administered to a cell, tissue or subject, as described herein. In certain embodiments, at least about 5, 10, 15, 20, 25, 50, 75, 100, 150, 200, 250, 300, 350 amino acids, or more, including all intermediate lengths, are truncated from the N- and/or C-terminus of a full length GlyRS protein. Intermediate lengths are intended to include all integers there between, for example, 6, 7, 8, etc., 51, 52, 53, etc., 201, 202, 203, etc.

In certain illustrative embodiments, truncated GlyRS polypeptides may be produced using any of a variety of proteolytic enzymes using techniques known and available in the art. Illustrative proteases include, for example, achromopeptidase, aminopeptidase, ancrod, angiotensin converting enzyme, bromelain, calpain, calpain I, calpain II, carboxypeptidase A, carboxypeptidase B, carboxypeptidase G, carboxypeptidase P, carboxypeptidase W, carboxypeptidase Y, caspase 1, caspase 2, caspase 3, caspase 4, caspase 5, caspase 6, caspase 7, caspase 8, caspase 9, caspase 10, caspase 11, caspase 12, caspase 13, cathepsin B, cathepsin C, cathepsin D, cathepsin E, cathepsin G, cathepsin H, cathepsin L, chymopapain, chymase, chymotrypsin, clostripain, collagenase, complement C1r, complement C1s, complement Factor D, complement factor I, cucumisin, dipeptidyl peptidase IV, elastase (leukocyte), elastase (pancreatic), endoproteinase Arg-C, endoproteinase Asp-N, endoproteinase Glu-C, endoproteinase Lys-C, enterokinase, factor Xa, ficin, furin, granzyme A, granzyme B, HIV Protease, IGase, kallikrein tissue, leucine aminopeptidase (general), leucine aminopeptidase (cytosol), leucine aminopeptidase (microsomal), matrix metalloprotease, methionine aminopeptidase, neutrase, papain, pepsin, plasmin, prolidase, pronase E, prostate specific antigen, protease alkalophilic from *Streptomyces griseus*, protease from *Aspergillus*, protease from *Aspergillus saitoi*, protease from *Aspergillus sojae*, protease (*B. licheniformis*) (alkaline or alcalase), protease from *Bacillus polymyxa*, protease from *Bacillus sp*, protease from *Rhizopus sp.*, protease S, proteasomes, proteinase from *Aspergillus oryzae*, proteinase 3, proteinase A, proteinase K, protein C, pyroglutamate aminopeptidase, rennin, rennin, streptokinase, subtilisin, thermolysin, thrombin, tissue plasminogen activator, trypsin, tryptase and urokinase.

In certain embodiments, the present invention provides variants of the GlyRS polypeptides described herein. Polypeptide variants encompassed by certain illustrative embodiments of the present invention will typically exhibit at least about 70%, 75%, 80%, 85%, 90%, 91%, 92%, 93%, 94%, 95%, 96%, 97%, 98%, or 99% identity (determined as described below), along their lengths, to the corresponding region of a wild-type GlyRS protein, such as SEQ ID NO: 1.

A polypeptide variant may differ from a naturally occurring GlyRS polypeptide in one or more substitutions, deletions, additions and/or insertions. Such variants may be naturally occurring or may be synthetically generated, for example, by modifying one or more of the above polypeptide sequences of the invention and evaluating their biological activity as described herein using any of a number of techniques well known in the art.

In other illustrative embodiments, the GlyRS variant may be a splice variant, whether naturally or non-naturally occurring, wherein the splice variant possesses at least one non-canonical activity, e.g., as described herein.

In other illustrative embodiments, the variant contains one or more point mutations relative to a wild type GlyRS polypeptide sequence, whether naturally or non-naturally occurring, wherein the variant polypeptide possesses at least one non-canonical activity, e.g., as described herein.

In certain embodiments, a variant will contain conservative substitutions. A "conservative substitution" is one in which an amino acid is substituted for another amino acid that has similar properties, such that one skilled in the art would expect the secondary structure and hydropathic nature of the polypeptide to be substantially unchanged. Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant of a GlyRS polypeptide of the invention, one skilled in the art, for example, can change one or more of the codons of the encoding DNA sequence according to Table 1.

For example, certain amino acids may be substituted for other amino acids in a protein structure without appreciable loss of interactive binding capacity with structures such as, for example, receptors, antigen-binding regions of antibodies or binding sites on a substrate molecule. Since it is the interactive capacity and nature of a protein that generally defines that protein's biological functional activity, certain amino acid sequence substitutions can be made in a protein sequence, and, of course, its underlying DNA coding sequence, and nevertheless obtain a protein with like properties. It is thus contemplated that various changes may be made in the polypeptide sequences of the disclosed compositions, or corresponding DNA sequences which encode said polypeptides without appreciable loss of their desired utility or activity.

TABLE 1

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

In making such changes, the hydropathic index of amino acids may also be considered. The importance of the hydropathic amino acid index in conferring interactive biologic function on a protein is generally understood in the art (Kyte and Doolittle, 1982, incorporated herein by reference). For example, it is known that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1);

alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain non-conservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on secondary structure and hydropathic nature of the polypeptide.

Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted, for example, using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy-the Principles and Practice of Numerical Taxonomy*, Freeman Press, San Francisco, Calif.; Wilbur, W. J. and Lipman, D. J. (1983) *Proc. Nat'l Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Nat'l Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

Examples of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one illustrative approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

In certain embodiments of the invention, there are provided fusion polypeptides, and polynucleotides encoding fusion polypeptides. Fusion polypeptides refer to polypeptides of the invention that have been covalently linked, either directly or indirectly via an amino acid linker, to one or more heterologous polypeptide sequences (fusion partners). The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order.

The fusion partner may be designed and included for essentially any desired purpose provided they do not adversely effect the desired activity of the polypeptide. For example, in one embodiment, a fusion partner comprises a sequence that assists in expressing the protein (an expression enhancer) at higher yields than the native recombinant protein. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques. For example, DNA sequences encoding the polypeptide components of a desired fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures, if desired. Such a peptide linker sequence is incorporated into the fusion protein using standard techniques well known in the art. Certain peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39 46 (1985); Murphy et al., *Proc. Natl. Acad. Sci. USA* 83:8258 8262 (1986); U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located 5' to the DNA sequence encoding the first polypeptides. Similarly, stop codons required to end translation and transcription termination signals are present 3' to the DNA sequence encoding the second polypeptide.

In general, polypeptides and fusion polypeptides (as well as their encoding polynucleotides) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

In still other embodiments, a GlyRS polypeptide of the invention may be part of a dimer. Dimers may include, for example, homodimers between two identical GlyRS polypeptides, heterodimers between two different GlyRS polypeptides (e.g., a full-length GlyRS polypeptide and a truncated GlyRS polypeptide, or two different truncated GlyRS polypeptides), and/or heterodimers between a GlyRS polypeptide and a heterologous polypeptide. The monomers and/or dimers may be soluble and may be isolated or purified to homogeneity. Certain heterodimers, such as those between a GlyRS polypeptide and a heterologous polypeptide, may be bi-functional.

In other embodiments, a GlyRS polypeptide of the invention may be part of a multi-unit complex. A multi-unit complex of the present invention can include, for example, at least 2, 3, 4, or 5 or more monomers. The monomers and/or multi-unit complexes may be soluble and may be isolated or purified to homogeneity. Monomer units of a multi-unit complex may be different, homologous, substantially homologous, or identical to one another. However, a multi-unit complex of the invention includes at least one monomer comprising a GlyRS polypeptide as described herein or, in other embodiments, at least two or more GlyRS polypeptides, as described herein.

Covalently linked monomers can be linked directly (by bonds) or indirectly (e.g., via a linker). For directly linking the polypeptide monomers herein, it may be beneficial to modify the polypeptides herein to enhance dimerization or multimerization. For example, one or more amino acid residues of a GlyRS polypeptide may be modified by the addition or substitution by one or more cysteines. Methods for creating amino acid substitutions, such as cysteine substitutions, or other modifications to facilitate linking, are well known to those skilled in the art.

Certain embodiments of the present invention also contemplate the use of modified GlyRS polypeptides, including modifications that improve desired characteristics of a GlyRS polypeptide, as described herein. Illustrative modifications of GlyRS polypeptides of the invention include, but are not limited to, chemical and/or enzymatic derivatizations at one or more constituent amino acid, including side chain modifications, backbone modifications, and N- and C-terminal modifications including acetylation, hydroxylation, methylation, amidation, and the attachment of carbohydrate or lipid moieties, cofactors, and the like. Exemplary modifications also include pegylation of a GlyRS-polypeptide (see, e.g., Veronese and Harris, *Advanced Drug Delivery Reviews* 54: 453-456, 2002, herein incorporated by reference).

In certain aspects, chemoselective ligation technology may be utilized to modify truncated GlyRS polypeptides of the invention, such as by attaching polymers in a site-specific and controlled manner. Such technology typically relies on the incorporation of chemoselective anchors into the protein backbone by either chemical or recombinant means, and subsequent modification with a polymer carrying a complementary linker. As a result, the assembly process and the covalent structure of the resulting protein-polymer conjugate may be controlled, enabling the rational optimization of drug properties, such as efficacy and pharmacokinetic properties (see, e.g., Kochendoerfer, *Current Opinion in Chemical Biology* 9:555-560, 2005).

Polynucleotide Compositions

The present invention also provides isolated polynucleotides that encode the GlyRS polypeptides of the invention, as well as compositions comprising such polynucleotides.

As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be recognized by the skilled artisan, polynucleotides may be single-stranded (coding or antisense) or double-stranded, and may be DNA (genomic, cDNA or synthetic) or RNA molecules. Additional coding or noncoding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a GlyRS or a portion thereof) or may comprise a variant, or a biological functional equivalent of such a sequence. Polynucleotide variants may contain one or more substitutions, additions, deletions and/or insertions, as further described below, preferably such that the desired activity of the encoded polypeptide is not substantially diminished relative to the unmodified polypeptide. The effect on the activity of the encoded polypeptide may generally be assessed as described herein.

In additional embodiments, the present invention provides isolated polynucleotides comprising various lengths of contiguous stretches of sequence identical to or complementary to a glycyl-tRNA synthetase, wherein the isolated polynucleotides encode a GlyRS as described herein.

For example, polynucleotides are provided by this invention that encode at least about 5, 10, 15, 20, 25, 50, 75, 100, 150, 200, 250, 300, 350, 400, 450 or 500, or more, contiguous amino acid residues of a GlyRS polypeptide of the invention, as well as all intermediate lengths. It will be readily understood that "intermediate lengths", in this context, means any length between the quoted values, such as 101, 102, 103, etc.; 151, 152, 153, etc.; 201, 202, 203, etc.

In other embodiments, the present invention is directed to polynucleotides that are capable of hybridizing under moderately stringent conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

The polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed, with the total length preferably being limited by the ease of preparation and use in the intended recombinant DNA protocol.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention, for example polynucleotides that are optimized for human and/or primate codon selection. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides and fusions thereof may be prepared, manipulated and/or expressed using any of a variety of well established techniques known and available in the art. For example, polynucleotide sequences which encode polypeptides of the invention, or fusion proteins or functional equivalents thereof, may be used in recombinant DNA molecules to direct expression of a GlyRS polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, expression and/or activity of the gene product.

In order to express a desired polypeptide, a nucleotide sequence encoding the polypeptide, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke & Schuster, *J. Biol. Chem.* 264:5503 5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH may be used. For reviews, see Ausubel et al. (supra) and Grant et al., *Methods Enzymol.* 153:516-544 (1987).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in McGraw Hill, *Yearbook of Science and Technology*, pp. 191-196 (1992)).

An insect system may also be used to express a polypeptide of interest. For example, in one such system, Autographa californica nuclear polyhedrosis virus (AcNPV) is used as a vector to express foreign genes in *Spodoptera frugiperda* cells or in *Trichoplusia larvae*. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard et al., *Proc. Natl. Acad. Sci. U.S.A.* 91:3224-3227 (1994)).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *Proc. Natl. Acad. Sci. U.S.A.* 81:3655-3659 (1984)). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf et al., *Results Probl. Cell Differ.* 20:125-162 (1994)).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., *Cell* 11:223-232 (1977)) and adenine phosphoribosyltransferase (Lowy et al., *Cell* 22:817-823 (1990)) genes which can be employed in tk- or aprt-cells, respectively. Also, antimetabolite, antibiotic or herbicide resistance can be used as the basis for selection; for example, dhfr which confers resistance to methotrexate (Wigler et al., *Proc. Natl. Acad. Sci. U.S.A.* 77:3567-70 (1980)); npt, which confers resistance to the aminoglycosides, neomycin and G-418 (Colbere-Garapin et al., *J. Mol. Biol.* 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, *Proc. Natl. Acad. Sci. U.S.A.* 85:8047-51 (1988)). The use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., *Methods Mol. Biol.* 55:121-131 (1995)).

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., *Serological Methods, a Laboratory Manual* (1990) and Maddox et al., *J. Exp. Med.* 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins.

In addition to recombinant production methods, polypeptides of the invention, and fragments thereof, may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

According to another aspect of the invention, polynucleotides encoding polypeptides of the invention may be delivered to a subject in vivo, e.g., using gene therapy techniques. Gene therapy refers generally to the transfer of heterologous nucleic acids to the certain cells, target cells, of a mammal, particularly a human, with a disorder or conditions for which such therapy is sought. The nucleic acid is introduced into the selected target cells in a manner such that the heterologous DNA is expressed and a therapeutic product encoded thereby is produced.

Various viral vectors that can be utilized for gene therapy as taught herein include adenovirus, herpes virus, vaccinia, adeno-associated virus (AAV), or, preferably, an RNA virus such as a retrovirus. Preferably, the retroviral vector is a derivative of a murine or avian retrovirus, or is a lentiviral vector. The preferred retroviral vector is a lentiviral vector. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of additional retroviral vectors can incorporate multiple genes. All of these vectors can transfer or incorporate a gene for a selectable marker so that transduced cells can be identified and generated. By inserting a zinc finger derived-DNA binding polypeptide sequence of interest into the viral vector, along with another gene that encodes the ligand for a receptor on a specific target cell, for example, the vector may be made target specific. Retroviral vectors can be made target specific by inserting, for example, a polynucleotide encoding a protein (dimer). Illustrative targeting may be accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the zinc finger-nucleotide binding protein polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsulation. Helper cell lines which have deletions of the packaging signal include but are not limited to PSI.2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

"Non-viral" delivery techniques for gene therapy can also be used including, for example, DNA-ligand complexes, adenovirus-ligand-DNA complexes, direct injection of DNA, $CaPO_4$ precipitation, gene gun techniques, electroporation, liposomes, lipofection, and the like. Any of these methods are widely available to one skilled in the art and would be suitable for use in the present invention. Other suitable methods are available to one skilled in the art, and it is to be understood that the present invention can be accomplished using any of the available methods of transfection. Lipofection can be accomplished by encapsulating an isolated DNA molecule within a liposomal particle and contacting the liposomal particle with the cell membrane of the target cell. Liposomes are self-assembling, colloidal particles in which a lipid bilayer, composed of amphiphilic molecules such as phosphatidyl serine or phosphatidyl choline, encapsulates a portion of the surrounding media such that the lipid bilayer surrounds a hydrophilic interior. Unilammellar or multilammellar liposomes can be constructed such that the interior contains a desired chemical, drug, or, as in the instant invention, an isolated DNA molecule.

Binding Agents and Modulators

According to another aspect, the present invention further provides binding agents and modulators, such as antibodies and antigen-binding fragments thereof, soluble receptors, dominant negative polypeptides, interfering RNAs, etc., that exhibit binding specificity for a GlyRS polynucleotide (including splice variant species) or polypeptide disclosed herein, or to a portion, variant or derivative thereof, and methods of using same. Preferably, such binding agents are effective for modulating one or more of the non-canonical activities mediated by a GlyRS polynucleotide or polypeptide of the invention, and thereby provide a desired cellular and/or therapeutic effect.

In certain embodiments, for example, the binding agent is one that binds to a GlyRS polynucleotide or polypeptide of the invention and modulates (e.g., inhibits or enhances) its ability to mediate one or more non-canonical activity of interest. For example, in some embodiments, the binding agent is one that binds to a GlyRS polynucleotide or polypeptide and modulates its ability to bind to one or more of its cellular binding partners. In other embodiments, the binding agent is one that binds to a GlyRS polynucleotide or polypeptide of the invention and modulates its expression and/or activity. Accordingly, such binding agents may be used to treat or prevent diseases, disorders or other conditions that are mediated by, or associated with, a GlyRS polynucleotide or polypeptide of the invention by modulating its activity.

In certain illustrative embodiments, the binding agent is an antibody or antigen-binding fragment thereof that specifically binds a GlyRS polypeptide of the invention. An antibody, or antigen-binding fragment thereof, is said to "specifically bind," "immunogically bind," and/or is "immunologically reactive" to a polypeptide of the invention if it reacts at a detectable level (within, for example, an ELISA assay) with the polypeptide, and does not react detectably with unrelated polypeptides under similar conditions.

etc. Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($k_{on}$) and the "off rate constant" ($k_{off}$) can be determined by calculation of the concentrations and the actual rates of association and dissociation. The ratio of $k_{off}/k_{on}$ enables cancellation of all parameters not related to affinity, and is thus equal to the dissociation constant $K_d$. See, generally, Davies et al. (1990) Annual Rev. Biochem. 59:439-473.

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

A binding agent may be, for example, a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) Proc. Nat. Acad. Sci. USA 69:2659-2662; Hochman et al. (1976) Biochem 15:2706-2710; and Ehrlich et al. (1980) Biochem 19:4091-4096.

A single chain Fv ("sFv") polypeptide is a covalently linked $V_H$::$V_L$ heterodimer which is expressed from a gene fusion including $V_H$- and $V_L$-encoding genes linked by a peptide-encoding linker. Huston et al. (1988) Proc. Nat. Acad. Sci. USA 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349:293-299; Lobuglio et al. (1989) Proc. Nat. Acad. Sci. USA 86:4220-4224; Shaw et al. (1987) J Immunol. 138:4534-4538; and Brown et al. (1987) Cancer Res. 47:3577-3583), rodent CDRs grafted into a human supporting FR prior to fusion with an appropriate human antibody constant domain (Riechmann et al. (1988) Nature 332:323-327; Verhoeyen et al. (1988) Science 239:1534-1536; and Jones et al. (1986) Nature 321:522-525), and rodent CDRs supported by recombinantly veneered rodent FRs (European Patent Publication No. 519,596, published Dec. 23, 1992). These "humanized" molecules are designed to minimize unwanted immunological response toward rodent antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) Ann. Rev. Biochem. 59:439-473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

In another embodiment of the invention, monoclonal antibodies of the present invention may be coupled to one or more agents of interest. For example, a therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used.

In other aspects of the invention, modulators/binding agents according to the present invention can comprise one or more interfering RNA (RNAi) sequences specific for a GlyRS polynucleotide. RNA interference methods using interfering RNAi molecules may be used to disrupt the expression of a desired gene or polynucleotide of interest, such as a GlyRS gene or splice variant in order to achieve a desired cellular and/or therapeutic effect.

In particular embodiments, the interfering RNA is a small interfering RNA (siRNA). siRNAs are RNA duplexes typically 19-30 nucleotides long that can associate with a cytoplasmic multi-protein complex known as RNAi-induced silencing complex (RISC). RISC loaded with siRNA mediates the degradation of homologous mRNA transcripts. Therefore, siRNA can be designed to knock down protein expression with high specificity. While the first described RNAi molecules were RNA:RNA hybrids comprising both an RNA sense and an RNA antisense strand, it has now been demonstrated that DNA sense:RNA antisense hybrids, RNA sense:DNA antisense hybrids, and DNA:DNA hybrids are capable of mediating RNAi (Lamberton, J. S. and Christian, A. T., (2003) Molecular Biotechnology 24:111-119). Thus, the invention includes the use of RNAi molecules comprising any of these different types of double-stranded molecules. In addition, it is understood that RNAi molecules may be used and introduced to cells in a variety of forms. Accordingly, as used herein, RNAi molecules encompasses any and all molecules capable of inducing an RNAi response in cells, including, but not limited to, double-stranded polynucleotides comprising two separate strands, i.e. a sense strand and an antisense strand, e.g., small interfering RNA (siRNA); polynucleotides comprising a hairpin loop of complementary sequences, which forms a double-stranded region, e.g., small hairpin RNA (shRNA) molecules, and expression vectors that express one or more polynucleotides capable of forming a double-stranded polynucleotide alone or in combination with another polynucleotide.

RNAi molecules targeting specific GlyRS polynucleotides can be readily prepared according to procedures known in the art. Structural characteristics of effective siRNA molecules have been identified. Elshabir, S. M. et al. (2001) Nature 411:494-498 and Elshabir, S. M. et al. (2001), EMBO 20:6877-6888. Accordingly, one of skill in the art would understand that a wide variety of different siRNA molecules may be used to target a specific gene or transcript. In certain embodiments, siRNA molecules according to the invention are typically double-stranded and 16-30 or 18-25 nucleotides in length, including each integer in between. In one embodiment, a siRNA is about 21 nucleotides in length. In certain embodiments, siRNAs have 0-7 nucleotide 3' overhangs or 0-4 nucleotide 5' overhangs. In one embodiment, a siRNA molecule has a two nucleotide 3' overhang. In one embodiment, a siRNA is 21 nucleotides in length with two nucleotide 3' overhangs (i.e. they contain a 19 nucleotide complementary region between the sense and antisense strands). In certain embodiments, the overhangs are UU or dTdT 3' overhangs.

In one embodiment, siRNA target sites are selected by scanning the target mRNA transcript sequence for the occurrence of AA dinucleotide sequences. Each AA dinucleotide sequence in combination with the 3' adjacent approximately 19 nucleotides are potential siRNA target sites. In one embodiment, siRNA target sites are preferentially not located within the 5' and 3' untranslated regions (UTRs) or regions near the start codon (within approximately 75 bases), since proteins that bind regulatory regions may interfere with the binding of the siRNP endonuclease complex (Elshabir, S. et al. Nature 411:494-498 (2001); Elshabir, S. et al. EMBO J. 20:6877-6888 (2001)). In addition, potential target sites may be compared to an appropriate genome database, such as BLASTN 2.0.5, available on the NCBI server at www.ncbi.nlm, and potential target sequences with significant homology to other coding sequences eliminated.

In particular embodiments, the interfering RNA is a short hairpin RNA. ShRNAs contain a stem loop structure. In certain embodiments, they may contain variable stem lengths, typically from 19 to 29 nucleotides in length, or any number in between. In certain embodiments, hairpins contain 19 to 21 nucleotide stems, while in other embodiments, hairpins contain 27 to 29 nucleotide stems. In certain embodiments, loop size is between 4 to 23 nucleotides in length, although the loop size may be larger than 23 nucleotides without significantly affecting silencing activity. ShRNA molecules may contain mismatches, for example G-U mismatches between the two strands of the shRNA stem without decreasing potency. In fact, in certain embodiments, shRNAs are designed to include one or several G-U pairings in the hairpin stem to stabilize hairpins during propagation in bacteria, for example. However, complementarity between the portion of the stem that binds to the target mRNA (antisense strand) and the mRNA is typically required, and even a single base pair mismatch is this region may abolish silencing. 5' and 3' overhangs are not required, although they may be present.

In certain aspects, an interfering RNA or siRNA comprises one or more modifications, such as a modified nucleoside or a modified phosphate linkage. In one embodiment, a siRNA comprises at least one modified nucleotide in the double-stranded region. In some embodiments, the modified siRNA contains at least one 2'OMe purine or pyrimidine nucleotide such as a 2'OMe-guanosine, 2'OMe-uridine, 2'OMe-adenosine, and/or 2'OMe-cytosine nucleotide. Examples of modified nucleotides suitable for use in the present invention include, but are not limited to, ribonucleotides having a 2'-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl group.

Non-limiting examples of phosphate backbone modifications (i.e., resulting in modified internucleotide linkages) that may be present in interfering RNA of the present invention include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al., *Nucleic Acid Analogues: Synthesis and Properties*, in *Modern Synthetic Methods*, VCH, 331-417 (1995); Mesmaeker et al., *Novel Backbone Replacements for Oligonucleotides*, in *Carbohydrate Modifications in Antisense Research*, ACS, 24-39 (1994)). Such chemical modifications can occur at the 5'-end and/or 3'-end of the sense strand, antisense strand, or both strands of the siRNA.

In particular embodiments, the interfering RNA targets a particular GlyRS mRNA expressed in a cell. Accordingly, the interfering RNA causes a reduction in expression of the targeted gene in the cell contacted with the interfering RNA. In particular embodiments, cells contacted with the interfering RNA under conditions and for a time sufficient for RNA interference to occur express less than 90%, less than 80%, less than 70%, less than 60%, less than 50%, less than 40%, less than 30%, less than 20%, or less than 10% the amount of the targeted gene as expressed by the same cell type not contacted with the interfering RNA. Expression may be measured as either protein expression or mRNA expression, or as microRNA expression. Levels of the protein expressed by the target gene may be readily determined using routine procedures, e.g., such as Western blotting or FACS. Levels of RNA expressed by a targeted gene may be readily determined using routine procedures such as RT-PCR.

An interfering RNA used in the present invention comprises a region corresponding to or complementary to a region of a target GlyRS gene. In preferred embodiments, this complementary region is completely complementary, while in other embodiments, it may comprise one or more mismatches. In certain embodiments, the complementary region is between 19 and 25 bases in length or between 19 and 21 bases in length.

Also included in modulators/binding agents of the invention are, for example, dominant negative forms of a GlyRS polypeptide, such as a mutant and/or truncated GlyRS polypeptide that can bind a GlyRS polypeptide of the invention and interfere with or antagonize one or more of its non-canonical activities.

Formulation and Administration

The compositions of the invention (e.g., polypeptides, polynucleotides, antibodies, etc.) are generally formulated in pharmaceutically-acceptable or physiologically-acceptable solutions for administration to a cell, tissue or animal, either alone, or in combination with one or more other modalities of therapy. It will also be understood that, if desired, the compositions of the invention may be administered in combination with other agents as well, such as, e.g., other proteins or polypeptides or various pharmaceutically-active agents. There is virtually no limit to other components that may also be included in the compositions, provided that the additional agents do not adversely affect properties of a GlyRS polypeptide of the invention.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intracranial and intramuscular administration and formulation.

In certain applications, the pharmaceutical compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein parenterally, intravenously, intramuscularly, or even intraperitoneally as described, for example, in U.S. Pat. No. 5,543,158; U.S. Pat. No. 5,641,515 and U.S. Pat. No. 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences*, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the pharmaceutical compositions may be delivered by intranasal sprays, inhalation, and/or other aerosol delivery vehicles. Methods for delivering genes, polynucleotides, and peptide compositions directly to the lungs via nasal aerosol sprays has been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

Kits Comprising Compositions of the Invention

The invention, in other aspects, provides kits comprising one or more containers filled with one or more of the polypeptides, polynucleotides, antibodies, multiunit complexes, compositions thereof, etc., of the invention, as described herein. The kits can include written instructions on how to use such compositions (e.g., to modulate cellular signaling, angiogenesis, cancer, inflammatory conditions, etc.).

The kits herein may also include a one or more additional therapeutic agents or other components suitable or desired for the indication being treated. An additional therapeutic agent may be contained in a second container, if desired. Examples of additional therapeutic agents include, but are not limited to antineoplastic agents, anti-inflammatory agents, antibacterial agents, antiviral agents, angiogenic agents, etc.

The kits herein can also include one or more syringes or other components necessary or desired to facilitate an intended mode of delivery (e.g., stents, implantable depots, etc.).

Methods of Use

In another aspect, the present invention relates to methods of using the compositions of the present invention (e.g., polynucleotides, polypeptides, etc.), or binding agents or other modulators of such compositions (e.g., antibodies, interfering RNAs, antisense RNAs, dominant negative polypeptides, small molecule modulators, etc.) for treating a cell, tissue or subject in order to achieve a desired cellular and/or therapeutic effect. The cells or tissues that may be modulated by the present invention are preferably mammalian cells or tissues, or more preferably human cells or tissues. Such cells or tissues can be of a healthy state or of a diseased state.

In certain embodiments, for example, methods are provided for modulating therapeutically relevant cellular activities by contacting a cell with a GlyRS composition as described herein. Such cellular activities can include, but not limited to, cellular metabolism, cell differentiation, cell proliferation, cell death, cell mobilization, cell migration, cell signaling, modulation of cytokine production and/or secretion, gene transcription, mRNA translation, cell impedence, and the like. In more specific embodiments, cellular activities to be modulated according to the present invention include, for example, Akt-mediated cell signaling, Erk1/2-mediated cell signaling, GPCR-mediated cell signaling, endothelial cell tube formation, and cell binding. In other specific embodiments, cellular activities include, for example, modulation of CD71 and/or CD80. In yet other specific embodiments, cellular activities include, for example, modulation of cytokine production and/or release, wherein the cytokine is selected from the group consisting of TNF-$\alpha$, IL1-$\beta$, IL-6, IL-8, IL-10, IL-12p40, MIP1-$\alpha$, MIP-1$\beta$, GRO-$\alpha$, MCP-1 and IL-1ra. In yet other specific embodiments, cellular activities include, for example, metabolic regulation through modulation of cellular glucose, glucagon, glycerol and/or free fatty acid. In yet other specific embodiments, cellular activities include, for example, modulation of neurogenesis or neuroprotection. Accordingly, the GlyRS compositions may be employed in treating essentially any cell or tissue or subject that would benefit from modulation of one or more such activities.

The GlyRS compositions may also be used in any of a number of therapeutic contexts including, for example, those relating to the treatment or prevention of neoplastic diseases, immune system diseases (e.g., autoimmune diseases and inflammation), infectious diseases, metabolic diseases, neuronal/neurological diseases, muscular/cardiovascular diseases, diseases associated with aberrant hematopoiesis, diseases associated with aberrant angiogenesis, diseases associated with aberrant cell survival, and others.

For example, in certain illustrative embodiments, the GlyRS compositions of the invention may be used to modulate angiogenesis, e.g., via modulation of endothelial cell proliferation and/or signaling. Endothelial cell proliferation and/or signaling may be monitored using an appropriate cell line (e.g., human microvascular endothelial lung cells (HM-VEC-L) and human umbilical vein endothelial cells (HU-VEC)), and using an appropriate assay (e.g., endothelial cell migration assays, endothelial cell proliferation assays, tube-forming assays, matrigel plug assays, etc.), many of which are known and available in the art.

Therefore, in related embodiments, the compositions of the invention may be employed in the treatment of essentially any cell or tissue or subject that would benefit from modulation of angiogenesis. For example, in some embodiments, a cell or tissue or subject experiencing or susceptible to angiogenesis (e.g., an angiogenic condition) may be contacted with a suitable composition of the invention to inhibit an angiogenic condition. In other embodiments, a cell or tissue experiencing or susceptible to insufficient angiogenesis (e.g., an angiostatic condition) may be contacted with an appropriate composition of the invention in order to interfere with angiostatic activity and/or promote angiogenesis.

Illustrative examples of angiogenic conditions include, but are not limited to, age-related macular degeneration (AMD), cancer (both solid and hematologic), developmental abnormalities (organogenesis), diabetic blindness, endometriosis, ocular neovascularization, psoriasis, rheumatoid arthritis (RA), and skin discolorations (e.g., hemangioma, nevus flammeus or nevus simplex). Examples of anti-angiogenic conditions include, but are not limited to, cardiovascular disease, restenosis, tissue damage after reperfusion of ischemic tissue or cardiac failure, chronic inflammation and wound healing.

The compositions of the invention may also be useful as immunomodulators for treating anti- or pro-inflammatory indications by modulating the cells that mediate, either directly or indirectly, autoimmune and/or inflammatory diseases, conditions and disorders. The utility of the compositions of the invention as immunomodulators can be monitored using any of a number of known and available techniques in the art including, for example, migration assays (e.g., using leukocytes or lymphocytes) or cell viability assays (e.g., using B-cells, T-cells, monocytes or NK cells).

Illustrative immune system diseases, disorders or conditions that may be treated according to the present invention include, but are not limited to, primary immuodeficiencies, immune-mediated thrombocytopenia, Kawasaki syndrome, bone marrow transplant (for example, recent bone marrow transplant in adults or children), chronic B cell lymphocytic leukemia, HIV infection (for example, adult or pediatric HIV infection), chronic inflammatory demyelinating polyneuropathy, post-transfusion purpura, and the like.

Additionally, further diseases, disorders and conditions include Guillain-Barre syndrome, anemia (for example, anemia associated with parvovirus B19, patients with stable multiple myeloma who are at high risk for infection (for example, recurrent infection), autoimmune hemolytic anemia (for example, warm-type autoimmune hemolytic anemia), thrombocytopenia (for example, neonatal thrombocytopenia), and immune-mediated neutropenia, transplantation (for example, cytomegalovirus (CMV)-negative recipients of CMV-positive organs), hypogammaglobulinemia (for example, hypogammaglobulinemic neonates with risk factor for infection or morbidity), epilepsy (for example, intractable epilepsy), systemic vasculitic syndromes, myasthenia gravis (for example, decompensation in myasthenia gravis), dermatomyositis, and polymyositis.

Further autoimmune diseases, disorders and conditions include, but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (for example, IgA nephropathy), multiple sclerosis, neuritis, uveitis ophthalmia, polyendocrinopathies, purpura (for example, Henloch-Scoenlein purpura), Reiter's disease, stiff-man syndrome, autoimmune pulmonary inflammation, Guillain-Barre Syndrome, insulin dependent diabetes mellitis, and autoimmune inflammatory eye disease.

Additional autoimmune diseases, disorders or conditions include, but are not limited to, autoimmune thyroiditis; hypothyroidism, including Hashimoto's thyroiditis and thyroiditis characterized, for example, by cell-mediated and humoral thyroid cytotoxicity; SLE (which is often characterized, for example, by circulating and locally generated immune complexes); Goodpasture's syndrome (which is often characterized, for example, by anti-basement membrane antibodies); pemphigus (which is often characterized, for example, by epidermal acantholytic antibodies); receptor autoimmunities such as, for example, Graves' disease (which is often characterized, for example, by antibodies to a thyroid stimulating hormone receptor) myasthenia gravis, (which is often characterized, for example, by acetylcholine receptor antibodies); insulin resistance (which is often characterized, for example, by insulin receptor antibodies); autoimmune hemolytic anemia (which is often characterized, for example, by phagocytosis of antibody-sensitized red blood cells); and autoimmune thrombocytopenic purpura (which is often characterized, for example, by phagocytosis of antibody-sensitized platelets).

Further autoimmune diseases, disorders or conditions include, but are not limited to, rheumatoid arthritis (which is often characterized, for example, by immune complexes in joints); scleroderma with anti-collagen antibodies (which is often characterized, for example, by nucleolar and other nuclear antibodies); mixed connective tissue disease, (which is often characterized, for example, by antibodies to extractable nuclear antigens, for example, ribonucleoprotein); polymyositis/dermatomyositis (which is often characterized, for example, by nonhistone anti-nuclear antibodies); pernicious anemia (which is often characterized, for example, by antiparietal cell, antimicrosome, and anti-intrinsic factor antibodies); idiopathic Addison's disease (which is often characterized, for example, by humoral and cell-mediated adrenal cytotoxicity); infertility (which is often characterized, for example, by antispennatozoal antibodies); glomerulonephritis (which is often characterized, for example, by glomerular basement membrane antibodies or immune complexes); primary glomerulonephritis, IgA nephropathy; bullous pemphigoid (which is often characterized, for example, by IgG and complement in the basement membrane); Sjogren's syndrome (which is often characterized, for example, by multiple tissue antibodies and/or the specific nonhistone antinuclear antibody (SS-B)); diabetes mellitus (which is often characterized, for example, by cell-mediated and humoral islet cell antibodies); and adrenergic drug resistance, including adrenergic drug resistance with asthma or cystic fibrosis (which is often characterized, for example, by beta-adrenergic receptor antibodies).

Still further autoimmune diseases, disorders or conditions include, but are not limited to chronic active hepatitis (which is often characterized, for example by smooth muscle antibodies); primary biliary cirrhosis (which is often characterized, for example, by anti-mitchondrial antibodies); other endocrine gland failure (which is characterized, for example, by specific tissue antibodies in some cases); vitiligo (which is often characterized, for example, by anti-melanocyte antibodies); vasculitis (which is often characterized, for example, by immunoglobulin and complement in vessel walls and/or low serum complement); post-myocardial infarction conditions (which are often characterized, for example, by anti-myocardial antibodies); cardiotomy syndrome (which is often characterized, for example, by anti-myocardial antibodies); urticaria (which is often characterized, for example, by IgG and IgM antibodies to IgE); atopic dermatitis (which is often characterized, for example, by IgG and IgM antibodies to IgE); asthma (which is often characterized, for example, by IgG and IgM antibodies to IgE); inflammatory myopathies; and other inflammatory, granulomatous, degenerative, and atrophic disorders.

In other embodiments, the GlyRS compositions of the invention may be used to modulate cellular proliferation and/or survival and, accordingly, for treating or preventing diseases, disorders or conditions characterized by abnormalities in cellular proliferation and/or survival. For example, in certain embodiments, the GlyRS compositions may be used to modulate apoptosis and/or to treat diseases or conditions associated with abnormal apoptosis. Apoptosis is the term used to describe the cell signaling cascade known as programmed cell death. Various therapeutic indications exist for molecules that induce apoptosis (e.g. cancer), as well as those that inhibit apoptosis (e.g. stroke, myocardial infarction, sepsis, etc.). Apoptosis can be monitored by any of a number of available techniques known and available in the art including, for example, assays that measure fragmentation of DNA, alterations in membrane asymmetry, activation of apoptotic caspases and/or release of cytochrome C and AIF.

Illustrative diseases associated with increased cell survival, or the inhibition of apoptosis include, but are not limited to, cancers (such as follicular lymphomas, carcinomas, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Graves' disease, Hashimoto's thyroiditis, autoimmune diabetes, biliary cirrhosis, Behcet's disease, Crohn's disease, polymyositis, systemic lupus erythematosus and immune-related glomerulonephritis, autoimmune gastritis, autoimmune thrombocytopenic purpura, and rheumatoid arthritis), viral infections (such as herpes viruses, pox viruses and adenoviruses), inflammation, graft vs. host disease (acute and/or chronic), acute graft rejection, and chronic graft rejection.

Further illustrative diseases or conditions associated with increased cell survival include, but are not limited to, progression and/or metastases of malignancies and related disorders such as leukemia (including acute leukemias (for example, acute lymphocytic leukemia, acute myelocytic leukemia, including myeloblastic, promyelocytic, myelomonocytic, monocytic, and erythroleukemia)) and chronic leukemias (for example, chronic myelocytic (granulocytic) leukemia and chronic lymphocytic leukemia), myelodysplastic syndrome, polycythemia vera, lymphomas (for example, Hodgkin's disease and non-Hodgkin's disease), multiple myeloma, Waldenstrom's macroglobulinemia, heavy chain diseases, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Illustrative diseases associated with increased apoptosis include, but are not limited to, AIDS (such as HIV-induced nephropathy and HIV encephalitis), neurodegenerative disorders (such as Alzheimer's disease, Parkinson's disease, amyotrophic lateral sclerosis, retinitis pigmentosa, cerebellar degeneration and brain tumor or prior associated disease), autoimmune disorders such as multiple sclerosis, Sjogren's syndrome, Graves' disease, Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, rheumatoid arthritis, myelodysplastic syndromes (such as aplastic anemia), graft vs. host disease (acute and/or chronic), ischemic injury (such as that caused by myocardial infarction, stroke and reperfusion injury), liver injury or disease (for example, hepatitis related liver injury, cirrhosis, ischemia/reperfusion injury, cholestosis (bile duct injury) and liver cancer), toxin-induced liver disease (such as that caused by alcohol), septic shock, ulcerative colitis, cachexia, and anorexia.

In still further embodiments, the compositions of the invention may be used in the treatment of neuronal/neurological diseases or disorders, illustrative examples of which include Parkinson's disease, Alzheimer's disease, Pick's Disease, Creutzfeldt-Jacob disease, Huntington's chorea, alternating hemiplegia, amyotrophic lateral sclerosis, ataxia, cerebral palsy, chronic fatigue syndrome, chronic pain syndromes, congenital neurological anomalies, cranial nerve diseases, delirium, dementia, demyelinating diseases, dysautonomia, epilepsy, headaches, Huntington's disease, hydrocephalus, meningitis, movement disorders, muscle diseases, nervous system neoplasms, neurocutaneous syndromes, neurodegenerative diseases, neurotoxicity syndromes, ocular motility disorders, peripheral nervous system disorders, pituitary disorders, porencephaly, Rett syndrome, sleep disorders, spinal cord disorders, stroke, sydenham's chorea, tourette syndrome, nervous system trauma and injuries, etc.

Furthermore, additional embodiments relate to the use of the compositions of the invention in the treatment of metabolic disorders such as diabetes, obesity, cholesterol level regulation, adrenoleukodystrophy, Krabbe's disease (globoid cell leukodystrophy), metachromatic leukodystrophy, Alexander's disease, Canavan's disease (spongiform leukodystrophy), Pelizaeus-Merzbacher disease, Cockayne's syndrome, Hurler's disease, Lowe's syndrome, Leigh's disease, Wilson's disease, Hallervorden-Spatz disease, Tay-Sachs disease, etc. The utility of the compositions of the invention in modulating metabolic processes may be monitored using any of a variety of techniques known and available in the art including, for example, assays which measure adipocyte lipogenesis or adipocyte lipolysis.

In more specific embodiments of the invention, the GlyRS compositions of the invention are used to modulate G-protein coupled receptors (GPCRs). The GPCR receptor family consists of three main groups based on the G-protein that is coupled to the receptor (Gs, Gi and Gq). The Gs group is coupled to activation of adenylate cyclase production of cyclic AMP (cAMP), and the Gi group is coupled to inhibition of adenylate cyclase production of cAMP. Thus, assays to monitor accumulation of cAMP within cells upon treatment with GlyRS compositions of the invention can be used to monitor the activation of two primary groups of G-protein receptors.

In other specific embodiments, the GlyRS compositions of the invention may be used to modulate cellular signaling, for example, via kinase pathways (e.g., Akt, Erk1/2, and the like). Cell signaling may be monitored using any of a number of well known assays. For example, the induction of general cell signaling events can be monitored through altered phosphorylation patterns of a variety of target proteins. Detection of cell signaling activities in response to treatment of cells with GlyRS fragments therefore serves as an indicator of distinct biological effects. Target proteins used for this assay may be selected so as to encompass key components of major cellular signaling cascades, thereby providing a broad picture of the cell signaling landscape and its therapeutic relevance. Generally, such assays involve cell treatment with GlyRS polypeptides followed by immunodetection with antibodies that specifically detect the phosphorylated (activated) forms of the target proteins.

Illustrative target proteins used for monitoring therapeutically relevant cell signaling events may include, but are not limited to: p38 MAPK (mitogen-activated protein kinase; activated by cellular stress and inflammatory cytokines; involved in cell differentiation and apoptosis); SAPK/JNK (stress-activated protein kinase/Jun-amino-terminal kinase; activated by cellular stresses and inflammatory cytokines); Erk1/2, p44/42 MAPK (mitogen-activated protein kinase Erk1 and Erk2; activated by wide variety of extracellular signals; involved in regulation of cell growth and differentiation); and Akt (activated by insulin and various growth or survival factors; involved in inhibition of apoptosis, regulation of glycogen synthesis, cell cycle regulation and cell growth). General phosphorylation of tyrosine residues may also be monitored as a general indicator of changes in cell signaling mediated by phosphorylation.

Of course, it will be recognized that other classes of proteins, such as cell adhesion molecules (e.g., cadherins, integrins, claudins, catenins, selectins, etc.) and/or ion channel proteins may also be assayed for monitoring cellular events or activities modulated by the compositions of the invention.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLE 1

Generation of Human Glycyl-tRNA Synthetase (GlyrsRS) Fragments

Full-length recombinant human GlyRS having an amino acid sequence as set forth in SEQ ID NO: 1 was expressed and purified from *E. coli* using nickel IMAC chromatography. To generate fragments of GlyRS by controlled proteolysis, the full-length protein was treated with 167 nM human neutrophil elastase for 30 minutes before separation of the fragments by SDS-PAGE (FIGS. 1A-D).

EXAMPLE 2

GlyRS Fragments Activate Akt and GPCRs in Endothelial Cells

Pools of GlyRS fragments were generated by adding 25 ng neutrophil elastase to 4 ug full-length recombinant GlyRS for 30 minutes at 37° C. Reactions were stopped by the addition of alpha 1-antitrypsin (Serpin A1) in 10-fold excess of the protease. Bovine aortic endothelial cells (bAEC) were treated with pools of 50 nM full-length GlyRS protein uncleaved or cleaved with neutrophil elastase. Cells were incubated with GlyRS fragments for 10 minutes, harvested and subjected to western blotting with an antibody that specifically recognizes only the phosphorylated (activated) form of the signaling molecule Akt. This treatment resulted in strong, reproducible activation of Akt via phosphorylation (FIG. 2A). This effect is significant due to the role of Akt in inhibition of apoptosis, regulation of glycogen synthesis, cell cycle regulation, and cell growth.

The ability of the pool of GlyRS fragments generated by cleavage with neutrophil elastase to activate G-protein coupled receptors on endothelial cells was also assessed. The GPCR receptor family consists of three main groups based on the G-protein that is coupled to the receptor (Gs, Gi and Gq). The Gs group is coupled to activation of adenylate cyclase production of cyclic AMP (cAMP), and the Gi group is coupled to inhibition of adenylate cyclase production of cAMP. Thus, the accumulation of cAMP in endothelial cells in response to treatment with GlyRS fragments was assessed (Gs-GPCR signaling), as well as the ability of the fragments to inhibit forskolin-induced increases in cAMP (Gi-GPCR). Upon treatment of endothelial cells with 25 and 100 nM cleaved GlyRS fragments, a significant increase in the inhibition of forskolin-stimulated cAMP production was observed (~35% and ~40% respectively, FIG. 2B) as compared to treatment with 25 and 100 nM uncleaved GlyRS (~10%) over PBS alone, indicating activation of Gi-GPCRs. There was no stimulation of cAMP production upon treatment of endothelial cells with either uncleaved or cleaved GlyRS.

EXAMPLE 3

GlyRS Fragments Activate Erk1/2 (p44/42 MAPK) Signaling in Monocyte Cells

Pools of GlyRS fragments were generated by adding 25 ng neutrophil elastase to 4 ug full-length recombinant GlyRS for 30 minutes at 37° C. Reactions were stopped by the addition of alpha 1-antitrypsin (Serpin A1) in 10-fold excess of the protease. Monocytes (THP-1) were treated with pools of 50 nM full-length GlyRS protein uncleaved or cleaved with neutrophil elastase. Cells were incubated with GlyRS fragments for 0.5, 2, 5, 10, 30, and 60 minutes, harvested and subjected to western blotting with an antibody that specifically recognizes only the phosphorylated (activated) form of the signaling molecules Erk1/2 (mitogen-activated protein kinase Erk1 and Erk2). This treatment resulted in strong, reproducible activation of Erk1/2 via phosphorylation (FIG. 3) that was strongest after 2 minutes of treatment. This effect is significant due to the fact that Erk1/2 is activated by wide variety of extracellular signals, and plays a significant role in regulation of cell growth and differentiation.

EXAMPLE 4

Identification of Neutrophil Elastase Cleavage Sites on GlyRS

Fragments generated by cleavage with neutrophil elastase (FIG. 1D) were analyzed using LC/MS/MS to determine accurate masses for each fragment. In addition individual fragments were excised from an SDS-PAGE gel and subjected to in-gel trypsin digestion followed by LC/MS/MS analysis to identify the portion of the full-length protein from which the fragment was generated and to identify non-trypsin cleavage sites that could be attributed to neutrophil elastase.

The identity of these peptide boundaries is summarized in Table 1; residues in bold are non-trypsin cleavage sites indicating that the exact cleavage site of elastase (thus exact N- or C-terminus) of that fragment has been identified.

TABLE 1

| | | | | | |
|---|---|---|---|---|---|
| GlyRS peptide boundaries | | | | | |
| | Whole mass (Da) | Protease used | N-term, boundary | C-term, boundary | Non-tryptic peptide found |
| 1 | 71384 | No protease | A57 | E685 | |
| 2 | 50782 | No protease | P239 | E685 | PGYLRPETAQGIFLNFK (SEQ ID NO: 3) |

TABLE 1-continued

GlyRS peptide boundaries

| | Whole mass (Da) | Protease used | N-term, boundary | C-term, boundary | Non-tryptic peptide found |
|---|---|---|---|---|---|
| 3 | 53406 | elastase | T214 | E685 | TGNDLSPPVSFNLMFK (SEQ ID NO: 4) |
| 4 | 41000-43000 | elastase | F311-L338 | E685 | |
| 5 | 28096 | elastase | N439 | E685 | 439NVVQFEPSK (SEQ ID NO: 5) |
| 6 | 25328 | elastase | T214 | V438 | TGNDLSPPVSFNLMFK (SEQ ID NO: 4) 439NVVQFEPSK (SEQ ID NO: 5) |
| 7 | 22398 | elastase | T214 | R420 | TGNDLSPPVSFNLMFK (SEQ ID NO: 4) |
| 8 | 19783 | elastase | L511 | E685 | LYVEEVVPNVIEPSFGLGR (SEQ ID NO: 6) |
| 9 | | elastase | T214 | 325-338 | TGNDLSPPVSFNLMFK (SEQ ID NO: 4) |
| 10 | 4841 | elastase | A85 | T127 | AIYGGVSGLYDFGPVGCALK (SEQ ID NO: 7) QHFIQEEQILEIDCT (SEQ ID NO: 8) |
| 11 | 3675 | elastase | R25 | I56 | |

Figure 4A:
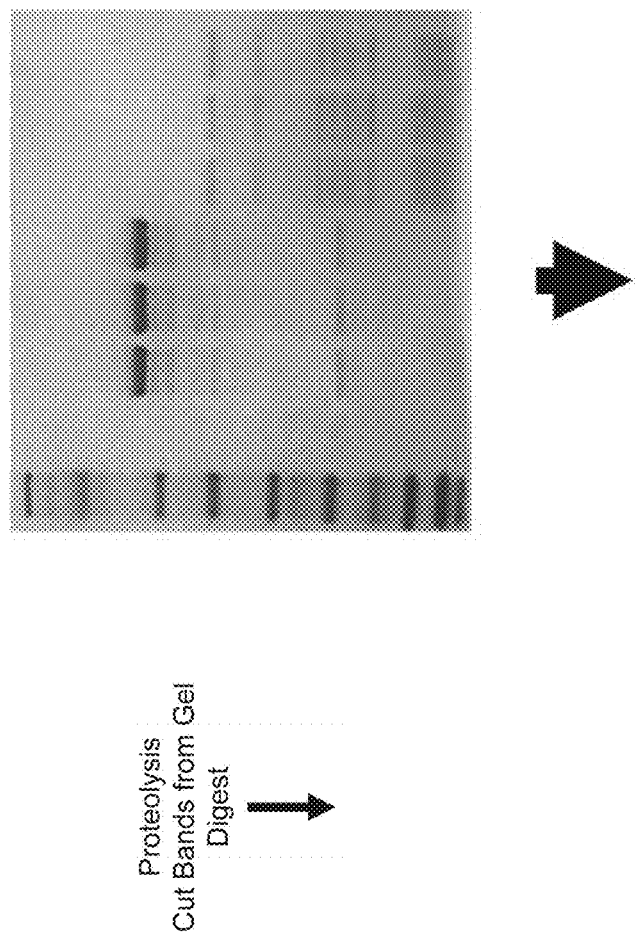
FIG. 4A depicts an overview of the process for analyzing GlyRS peptides (e.g., SEQ ID NO: 9) for determining GlyRS fragment boundaries.
Figure 4A:
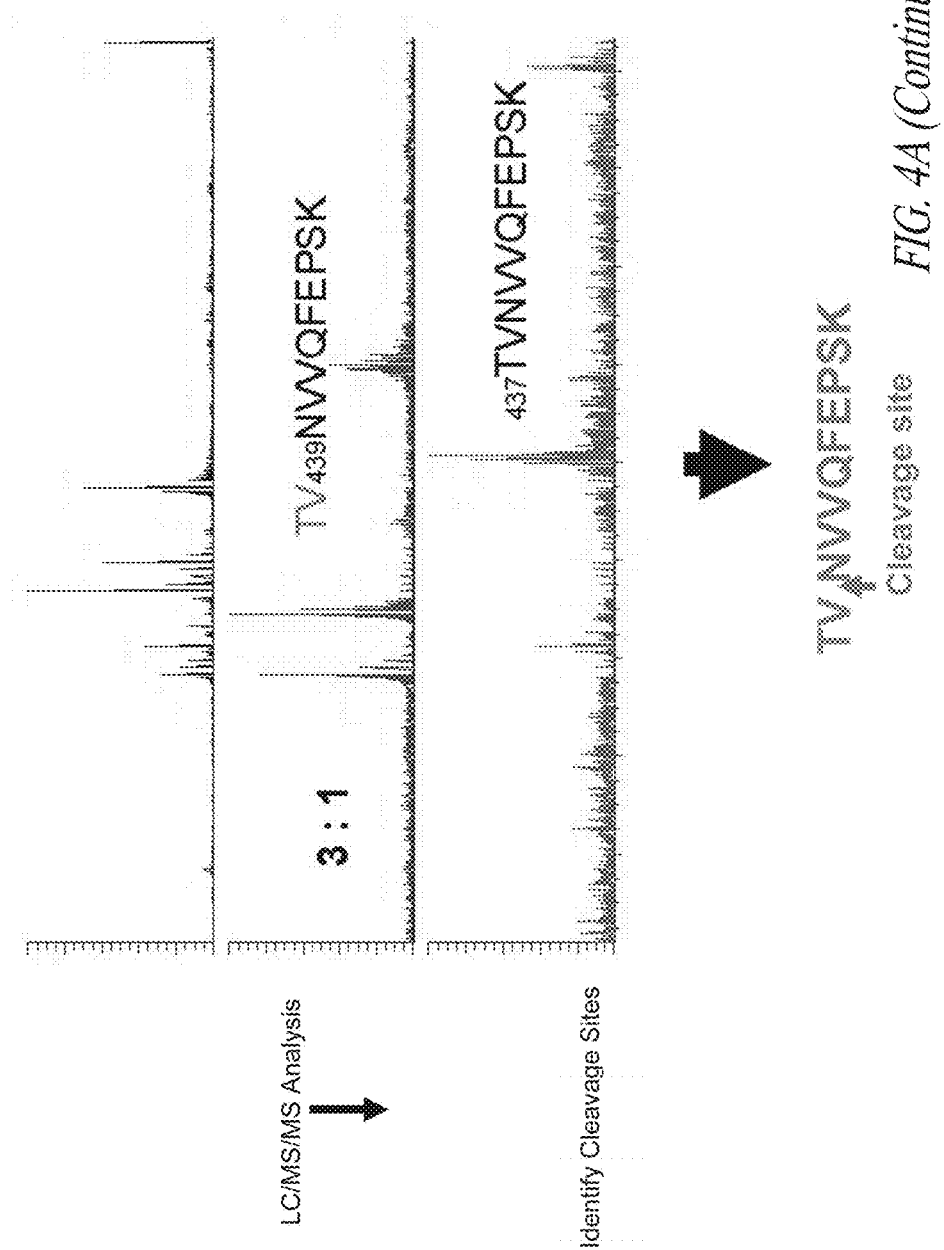
Figure 4B:
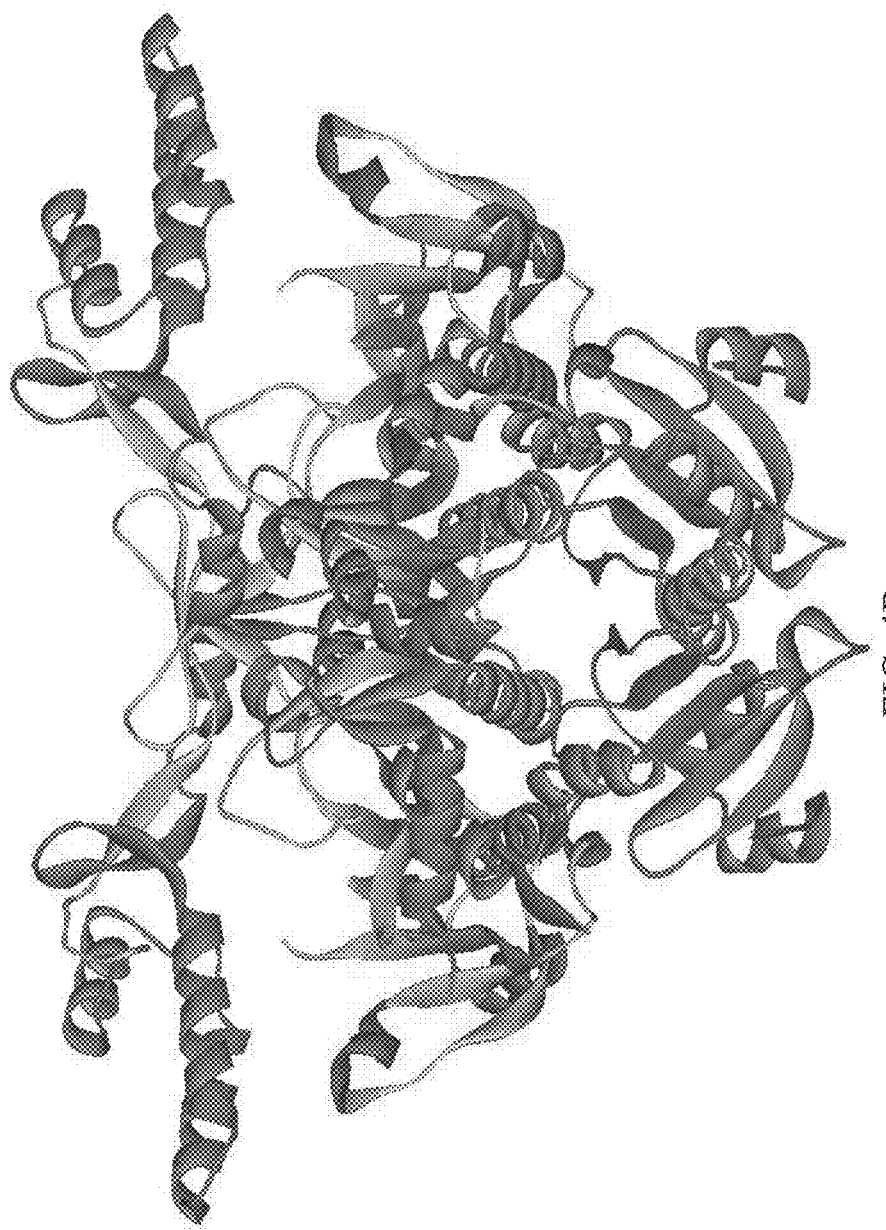
FIG. 4B shows the structure of the GlyRS fragment G6 corresponding to amino acids 214-438, within the crystal structure of full length human GlyRS dimer.

FIG. 4A depicts an overview of the above process for identifying GlyRS peptide boundaries. FIG. 4B shows an illustration of the structure of the GlyRS fragment G6, corresponding to amino acids 214-438, within the crystal structure of full length human GlyRS dimer.

EXAMPLE 5

GlyRS Fragment G6 Binds to Endothelial Cells

Full length GlyRS and GlyRS fragments were used in a binding assay on bAEC cells. Cells were split into 96-well plates at 30,000 cells/well overnight. The following day, media was removed and 50 ul/well Z-Fix was added to each well. Cells were incubated at room temperature for 15 minutes. Wells were aspirated and washed once with 1×PBST. Cells were blocked with 50 ul/well of 1% BSA/PBS for 1-2 hours at room temperature. The blocking solution was removed from the cells and protein samples diluted in 1% BSA/PBS were added to the wells. Samples were incubated at room temperature for 1 hour. Wells were washed once in 1×PBST. Anti-6×-His HRP (R&D #MAB050H) was added at 50 ul/well diluted 1:500 in 1% BSA/PBS. The antibody incubation lasted 30 minutes at room temperature. Wells were washed 3 times in 1×PBST. Protein binding was detected with 50 ul/well of a 1:1 dilution TMB solution (Thermo #34021). The reaction was quenched by the addition of 50 ul/well 2M sulfuric acid and absorbance was read at 405 nm on a plate reader.

Figure 5:
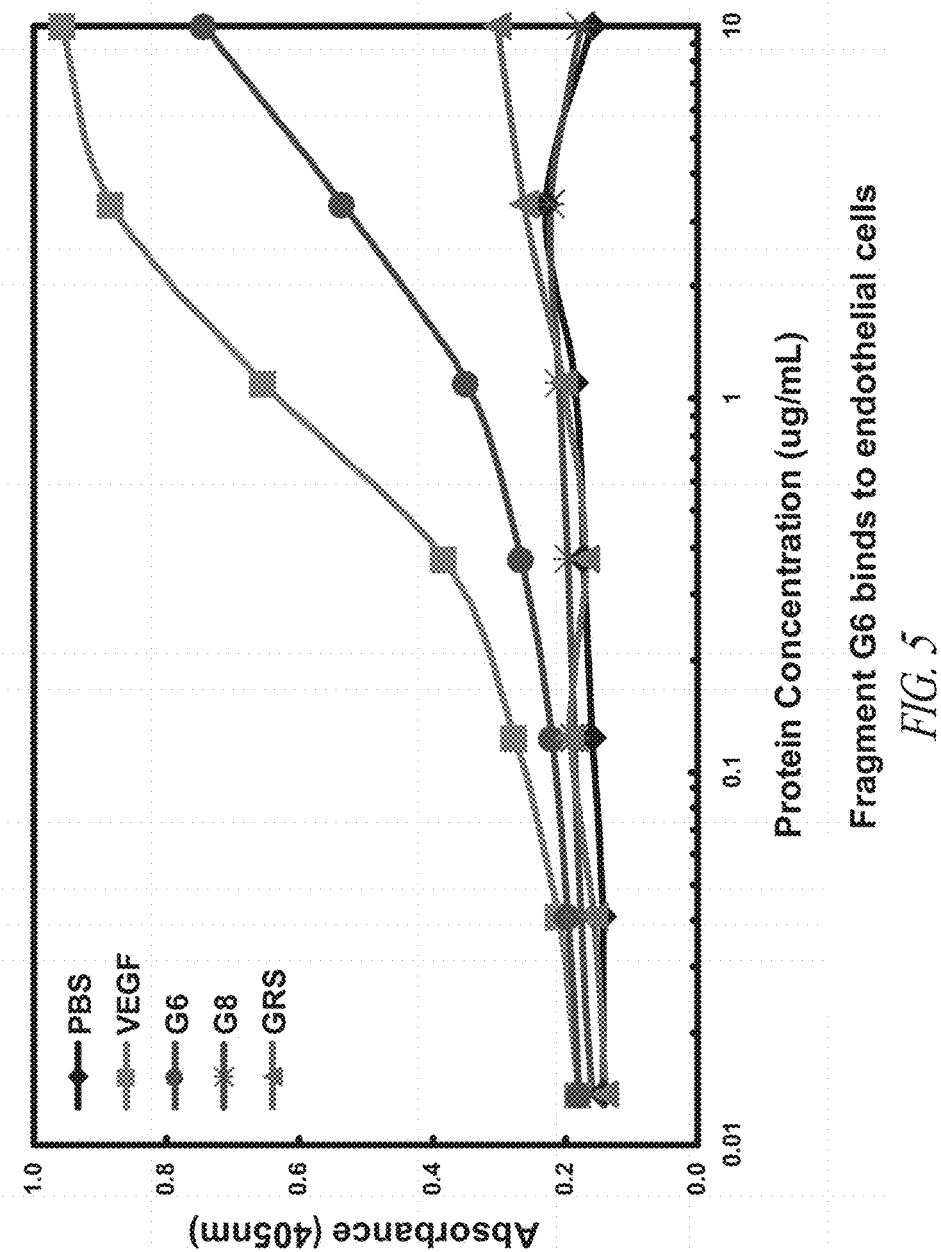
FIG. 5 shows that the GlyRS fragment G6, corresponding to amino acids 214-438, binds to endothelial cells.

The results of this study, as presented in FIG. 5, demonstrate that the GlyRS fragment G6, corresponding to amino acids 214-438, binds to endothelial cells.

EXAMPLE 6

A. GlyRS Fragment G6 Migrates THP-1 Monocytes and is Inhibited by Pertussis Toxin THP-1 monocyte cells were cultured in complete medium at $6\times10^5$ cells per well. Cells were washed with serum free media and incubated with Calcein AM (1 mg/ml) at a final concentration of 2 ug/ml. Cells were returned to the incubator for 30 minutes. Cells were washed again and plated into upper chamber of cell culture dishes at concentration of $6\times10^6$ cells/ml. Control chemokines as well as Fragment G6 (200 nM) were added to the lower chamber for 80 minutes to 2 hours. Cells were collected from the lower chamber by pipetting up and down. Fluorescence was read on a plate reader at Ex485/Em538 with 530 nm cutoff.

Figure 6:
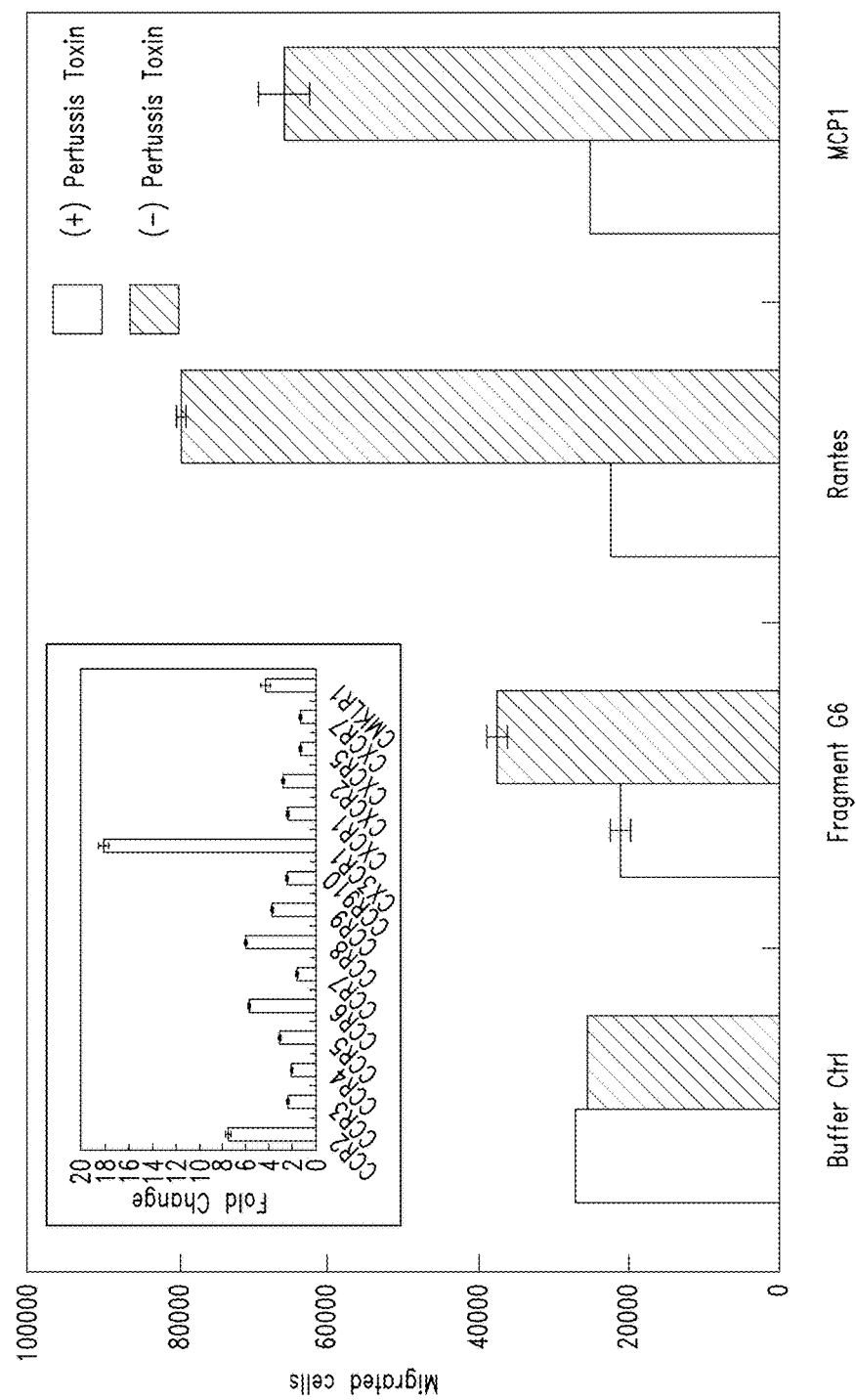
FIG. 6 demonstrates that GlyRS fragment G6 modulates migration of monocyte cells.

The results of this study, as shown in FIG. 6, demonstrate that G6 affects the migration monocyte cells.

B. GlyRS Fragment G6 Signals Through Select Chemokine Receptors

Chemokine receptor screening was performed using the PathHunter β-Arrestin assay (DiscoveRx Corporation) which monitors the activation of a GPCR in a homogenous, nonimaging assay format using a technology called complementation. This technology utilizes an enzyme fragment complementation (EFC) assay with β-galactosidase (β-Gal) as the functional reporter. The enzyme is split into two complementary portions expressed as fusion proteins in the cell. The Enzyme Acceptor (EA) is fused to β-Arrestin and the ProLink donor peptide is fused to the GPCR of interest. Upon GPCR stimulation, β-Arrestin is recruited to the receptor for desensitization, bringing the two fragments of β-Gal together and allowing complementation to occur. This generates an active enzyme that can convert a chemiluminescent substrate and generates an output signal detectable on a standard microplate reader. PathHunter cell lines were expanded from freezer stocks in T25 flasks according to standard procedures and maintained in selective growth media prior to assay. Once it was established that the cells were healthy and growing normally, cells were passaged from flasks using trypsin-free cell dissociation buffer and seeded into white walled clear bottom 384-well microplates for Fragment G6 profiling. For profiling, cells were seeded at a density of 5000 cells per well in a total volume of 20 µL and were allowed to adhere and recover overnight prior to Fragment G6 addition. Cells were incubated in the presence of 500 nM Fragment G6 at 37° C. for 90 minutes. Fifteen chemokine receptor cell lines were tested at 500 nM final concentration. Control wells contained 1% vehicle which was composed of 50% glycerol, 2 mM DTT, 0.5×PBS.

The results of this study, as shown in FIG. 6 (inset), demonstrate that GlyRS fragment G6 signals through select chemokine receptors.

EXAMPLE 7

Fragment G6 Affects Colony Formation of Megakaryocyte Progenitors

This study evaluated the effect of Fragment G6 (500 nM) on human megakaryocytic progenitor proliferation. Clonogenic progenitors of megakaryocyte (CFU-Mk) lineage were assessed in serum-free collagen-based medium Mega-Cult-C® 4950 supplemented with optimal proprietary concentrations of cytokines. Normal human bone marrow light density cells (Lonza lot #07B21195) were stored at −152° C. until required for the assay. On the day of the experiment, the cells were thawed rapidly at 37° C., the contents of the vial were diluted in 10 mL of Iscove's modified Dulbecco's medium (IMDM) containing 2% fetal bovine serum (FBS) and washed by centrifugation (1200 r.p.m. for 10 minutes, room temperature). The supernatant was discarded and the cell pellet resuspended in a known volume of IMDM containing 2% FBS. Fragment G6 was added to tubes of serum free collagen-based media MegaCult-C® 4950 supplemented with cytokines rhTpo, rhIL-3, and rhIL-6 at optimal proprietary concentrations. Buffer control cultures (containing no test protein but equivalent concentrations of dialyzed 50% glycerol 0.5×PBS/2 mM DTT buffer) were also initiated. Bone marrow cells were then added to each tube of media to give a final concentration of $1 \times 10^5$ cells per slide. Bovine collagen was then added, tubes were vortexed, and contents dispensed into triplicate double chamber slides. All cultures were incubated for 10-12 days at 37° C., 5% $CO_2$. Following incubation, cultures were assessed microscopically for colony formation prior to dehydration and fixation of the slide. Using an antibody staining protocol to detect GPIIa/IIIb (CD41) expression, the colonies on the slide were stained using an alkaline phosphatase detection system. Colony numbers were scored and assessed. The colonies were divided into the following categories, based on size and morphology; CFU-Mk small (2-20), CFU-Mk medium (21-49), CFU-Mk large (>50).

Figure 7A:
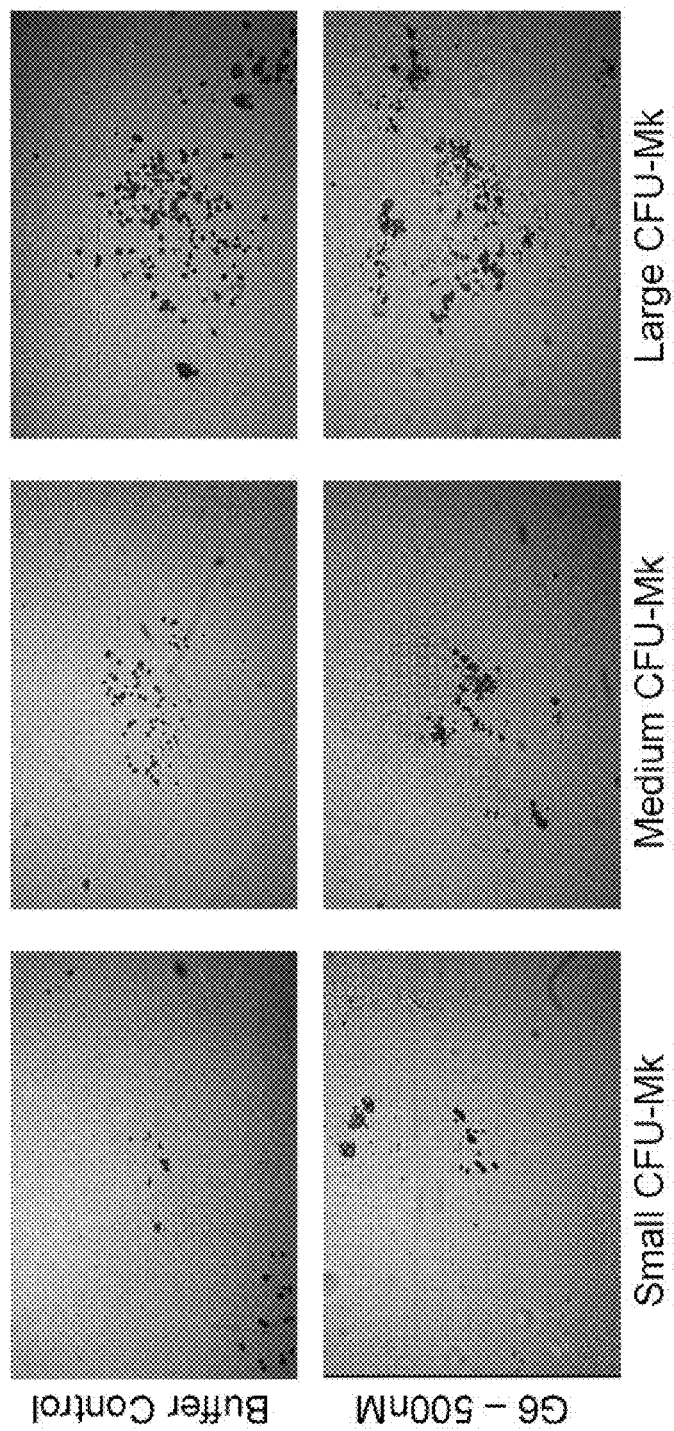
FIG. 7A shows representative stainings of CD41+ colonies.
Figure 7B:
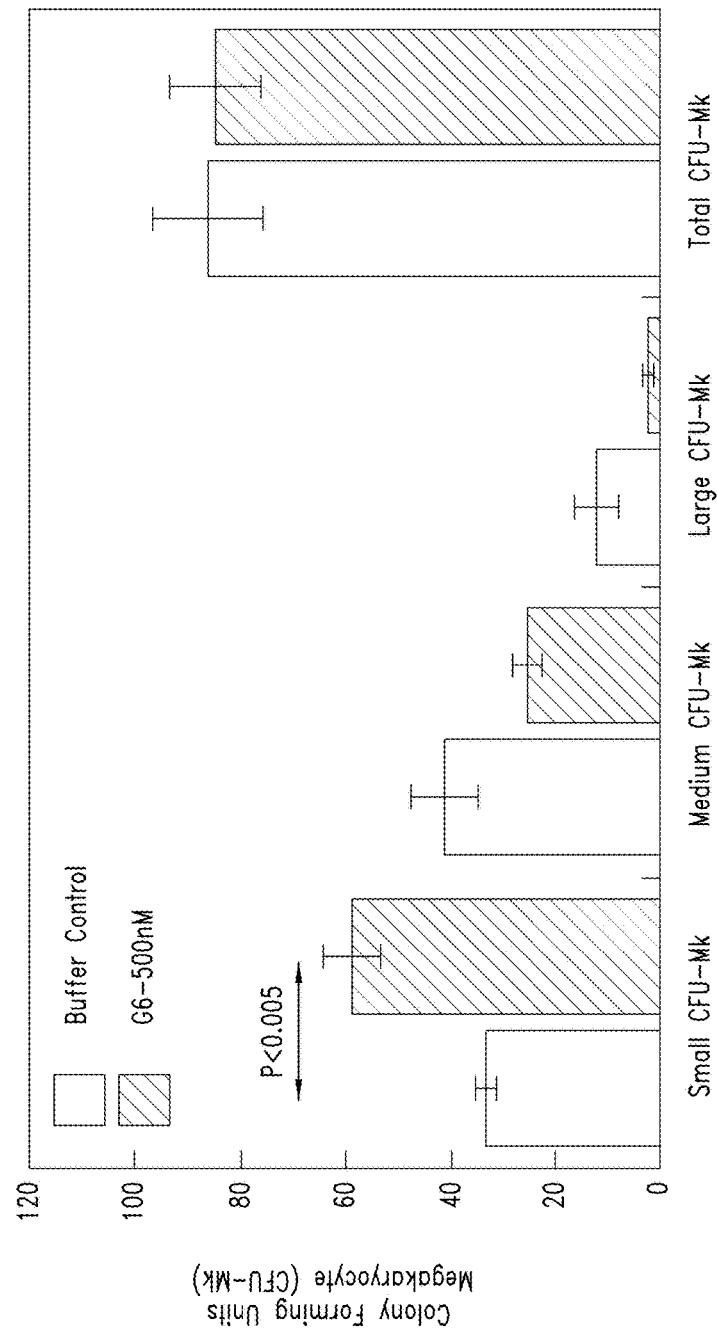
FIG. 7B shows the results of quantitation of small, medium and large colonies, and demonstrates that GlyRS fragment G6 affects colony formation of megakaryocyte progenitor cells.

FIG. 7A shows representative stainings of CD41+ colonies. FIG. 7B shows the results of quantitation of small, medium and large colonies. The results of this study demonstrate that GlyRS fragment G6 affects colony formation of megakaryocyte progenitor cells.

EXAMPLE 8

Fragments G6 and G6-3 Activate Monocytes

A. GlyRS Fragment Induces CD71 Marker Upregulation in Monocytes

Figure 8:
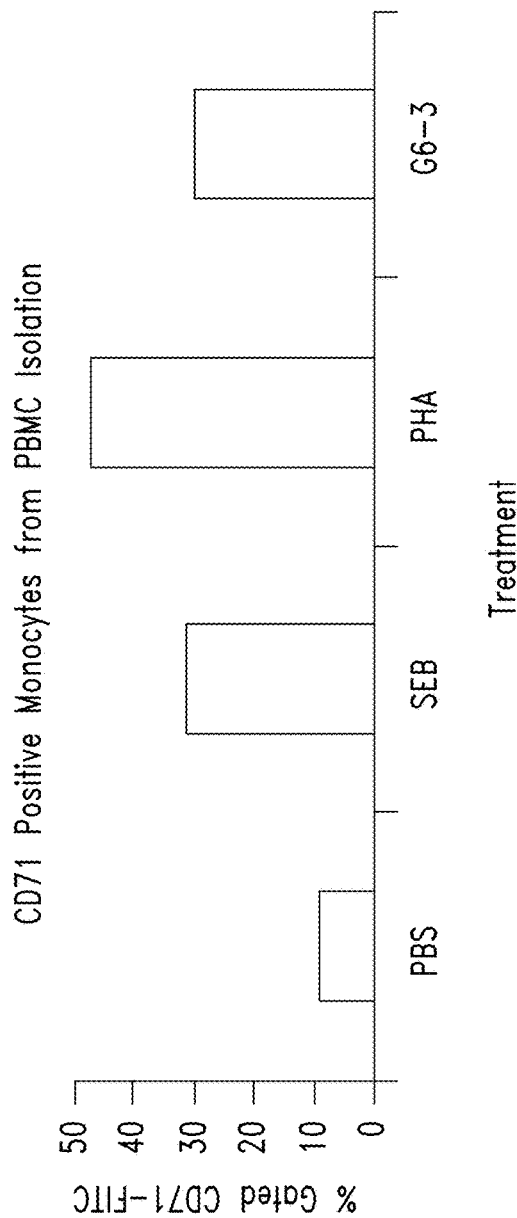
FIG. 8 shows upregulation of the CD71 proliferation marker in G6-3 treated monocytes after staining with anti-CD71-FITC antibody and analysis by flow cytometry.

Peripheral blood mononuclear cells (PBMC's) were isolated from a normal blood donor. $1.5 \times 10^6$ PBMC's were treated with a 200 nM dose of the GlyRS fragment G6-3 (consisting of residues 367-438) for 24 hours. PBMC's were treated with 1 ug/mL of the plant lectin phytohemagglutinin (PHA), and 0.1 ug/mL of the protein toxin *staphylococcal* enterotoxin B (SEB) as positive controls. As shown in FIG. 8, upregulation of the CD71 proliferation marker was seen in the G6-3 treated monocytes after staining with the anti-CD71-FITC antibody from Becton-Dickinson and analysis by flow cytometry. There was no significant increase in CD71 upregulation in the gated lymphocyte population of the same samples.

Thus, here we have demonstrated that G6-3 has a cell type specific ability to activate monocytes in a PBMC mixture.

B. GlyRS Fragment Induces CD80 Marker Upregulation in Monocytes

Figure 9:
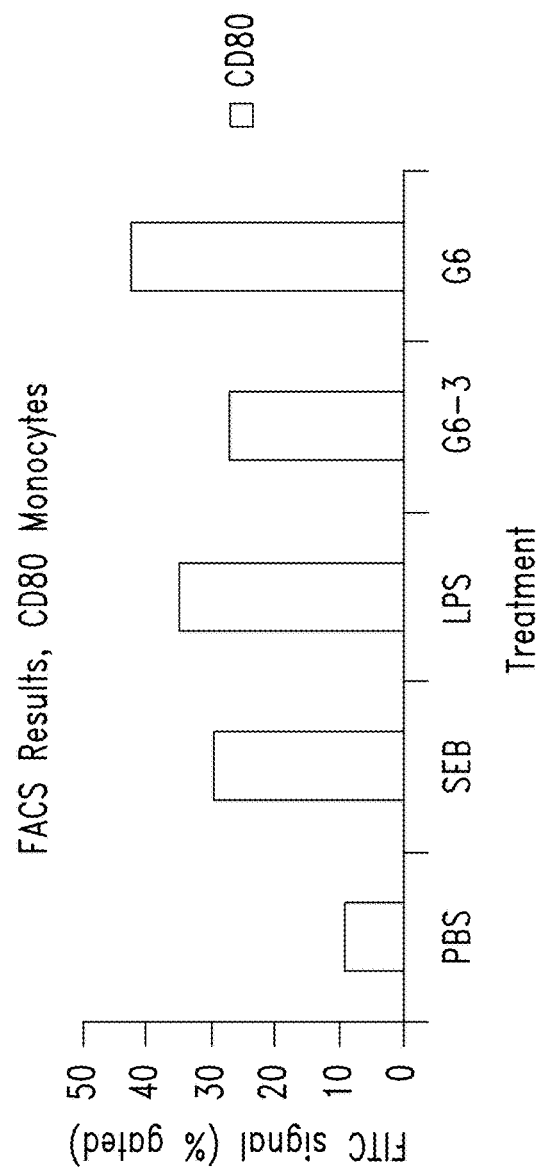
FIG. 9 shows upregulation of the CD80 activation marker in G6-3 treated monocytes after staining with anti-CD80-FITC antibody and analysis by flow cytometry.

Peripheral blood mononuclear cells (PBMC's) were isolated from a normal blood donor. $1.5 \times 10^6$ PBMC's were treated with a 200 nM dose of the GlyRS fragments G6 (consisting of residues 214-438) and G6-3 (367-438) for 24 hours. PBMC's were treated with 1 ug/mL of the plant lectin phytohemagglutinin (PHA), and 0.1 ug/mL of the protein toxin *staphylococcal* enterotoxin B (SEB) as positive controls. As shown in FIG. 9, upregulation of the CD80 activation marker was seen in the G6-3 treated monocytes after staining with the anti-CD80-FITC antibody from Becton-Dickinson and analysis by flow cytometry. There was no significant increase in CD80 upregulation in the gated lymphocyte population of the same samples.

The results of this study demonstrate that two GlyRS fragments, G6 and G6-3, activate monocytes in a PBMC mixture in cell type specific manner.

EXAMPLE 9

Figure 10:
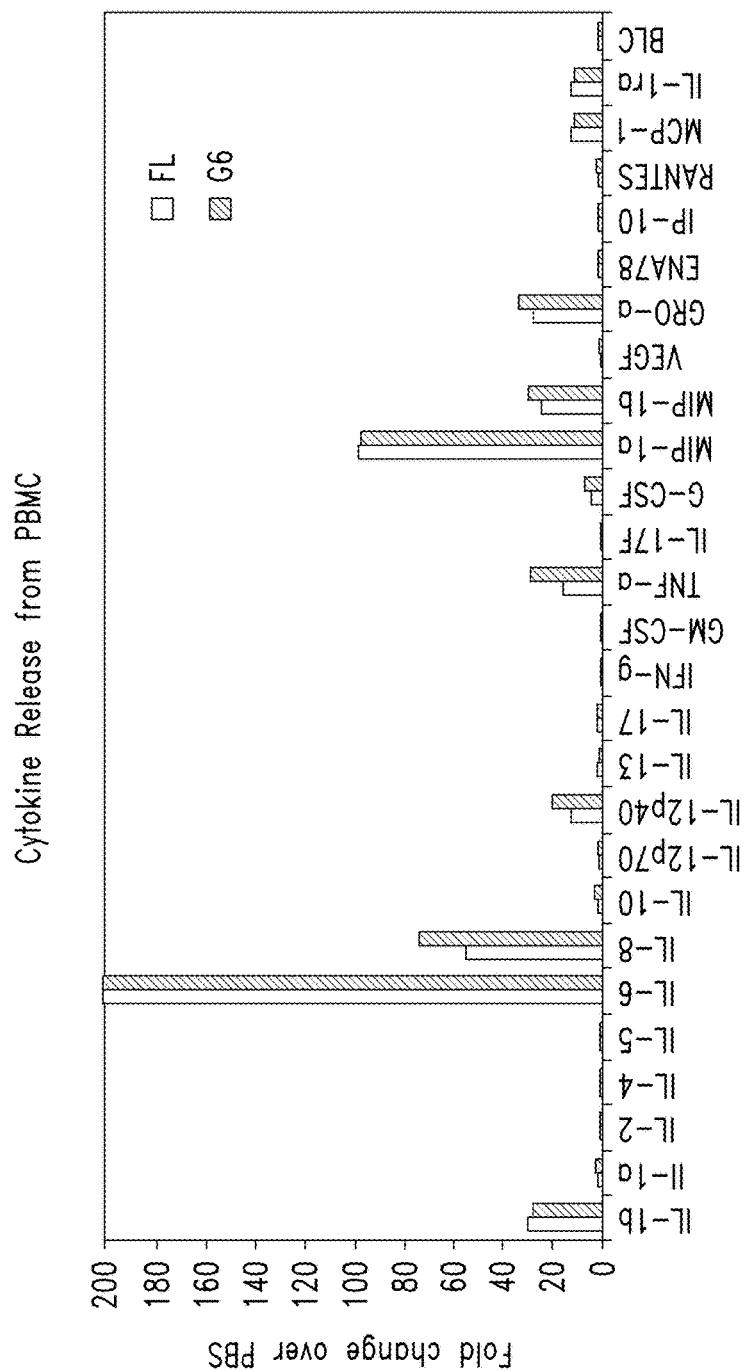
FIG. 10 shows that GlyRS and the G6 fragments stimulate secretion of numerous cytokines, including IL1-β, IL-6, IL-8, IL-10, IL-12p40, MIP1-α, MIP-1β, GRO-α, MCP-1, and IL-1ra.

Full-Length GlyRS and a Fragment of GlyRS G6 Induces Secretion of Cytokines from PBMCs Full length GlyRS (100 nM) or a fragment of GlyRS (residues 214-438), G6 (100 nM), were incubated with $1 \times 10^6$ Peripheral Blood Mononuclear Cells (PBMC) for 4 hours. After 4 hours of incubation, supernatants were harvested and snap frozen in liquid nitrogen. Samples were then analyzed by multiplex cytokine analysis (MD Biosciences; St. Paul, Minn.). Supernatants were measured for 27 distinct cytokines and graphed as fold change as compared to buffer-treated PBMC supernatants. Error bars are representative of 2 biological replicates. As shown in FIG. 10, both full-length GlyRS and the G6 fragment showed a large stimulation of numerous cytokines above cells treated with PBS (e.g., TNF-α, IL1-β, IL-6, IL-8, IL-10, IL-12p40, MIP1-α, MIP-1β, GRO-α, MCP-1, and IL-1ra).

The results of this study demonstrate that GlyRS polypeptides of the invention can induce secretion of multiple cytokines of therapeutic relevance.

EXAMPLE 10

Figure 11A:
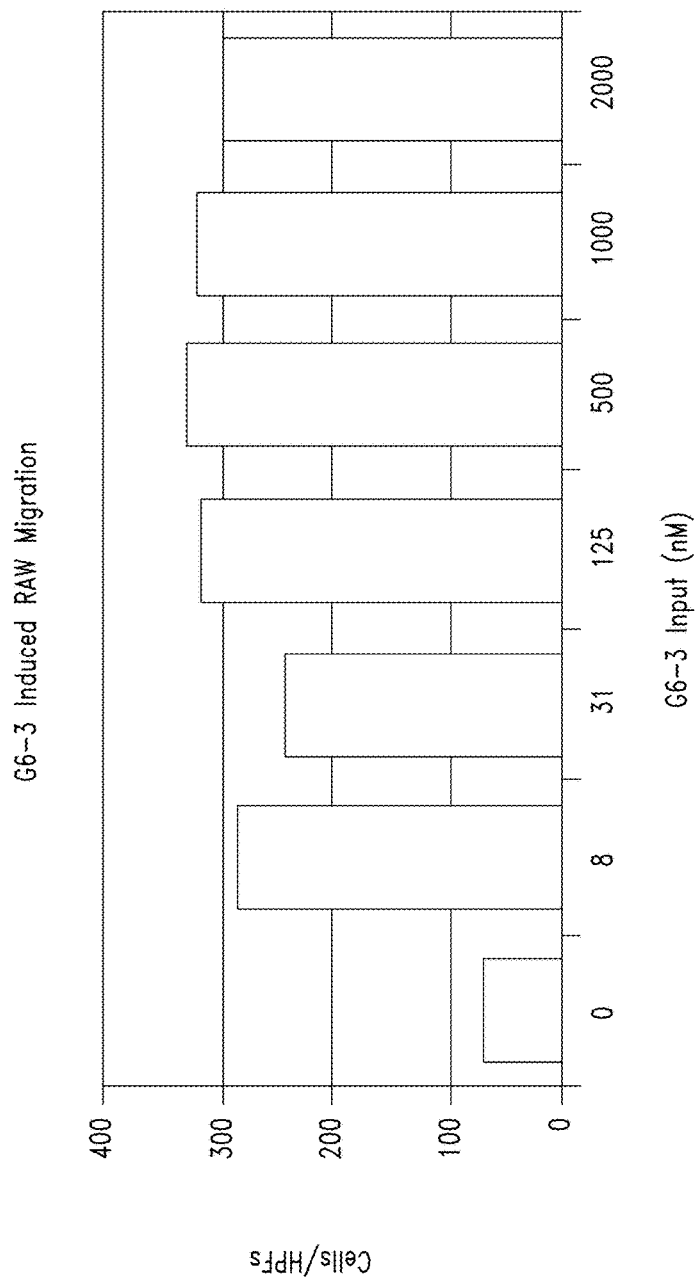
FIGS. 11A-11B show that GlyRS fragments G6 and G6-3 induce migration of mouse leukaemic macrophage cells.
Figure 11B:
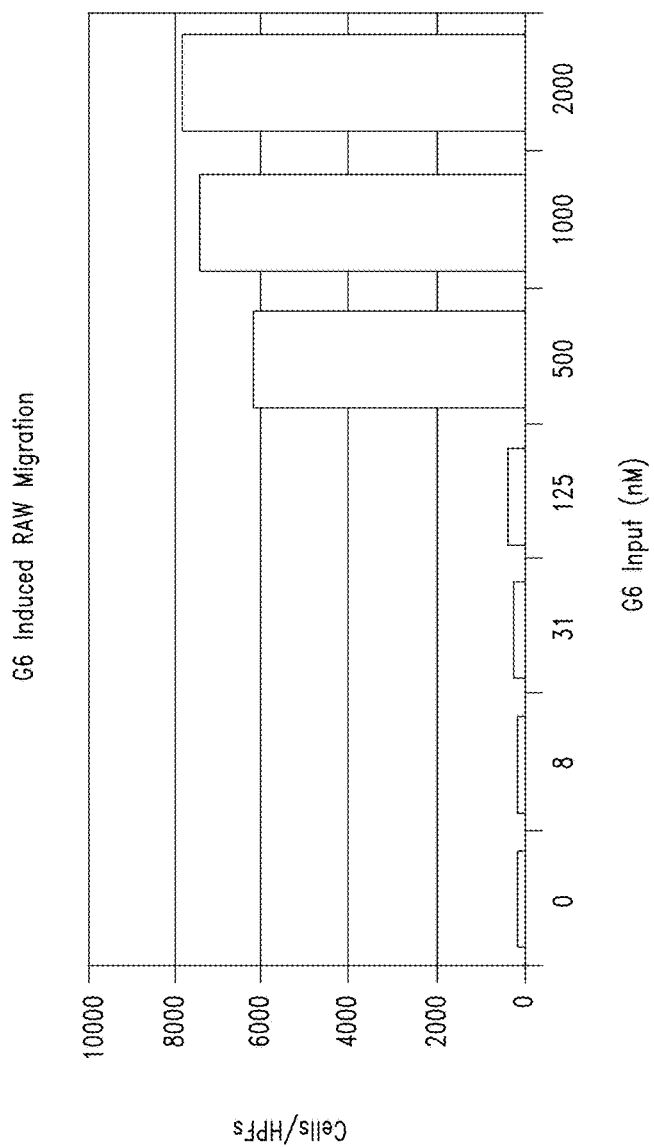

GlyRS Fragment G6 and G6-3 Induce Migration of RAW264.7 Mouse Leukaemic Macrophage Cells To assess cell migration in vitro, 24-well Transwell chambers with polycarbonate membranes (5 μm pore size, Costar) were coated with 0.5 mg/ml gelatin in PBS and allowed to air dry. Detached RAW264.7 cells (mouse monocyte/macrophage cell line) were washed once with fresh DMEM and suspended into $2 \times 10^7$ cells/ml with 0.1% BSA/DMEM. GlyRS fragments were diluted with 0.1% BSA/DMEM into different concentration as indicated in FIG. 11. RAW cells were placed to the upper chamber at $2 \times 10^6$ cells/100 ul/well. The lower chambers were filled with 500 ul/well with GlyRS fragment. After 24 hours, 37° C. migration, calcein AM (Invitrogen) was added to lower chambers into final 8 uM as cell indicator. 30 minutes later, nonmigrant cells were removed from the upper surface of the Transwell membrane with a cotton swab. Migrating cells on the lower membrane surface were counted under fluorescence microscope in high power fields.

The results of this study, as shown in FIG. 11, demonstrate that G6 and G6-3 can induce macrophage cell migration.

EXAMPLE 11

GlyLYRS Fragment G6 Induces Migration of HL-60 Promyelocytic Leukemia Cells

HL60 cells (human promyelocytic leukemia cell line) were washed twice with 0.1% BSA-RPMI. Calcein AM (Invitrogen) was added at 8 uM in 0.1% BSA-RPMI to incubate HL60 cells for 3 hours at 37 C. After one more time of wash, cells were suspended into $1 \times 10^7$ cells/ml with 0.1% BSA-RPMI. GRS or its fragment was diluted with 0.1% BSA-RPMI into different concentration as indicated in FIG. 11. HL60 cells were placed to the upper chamber of Transwell Permeable Support with polycarbonate membranes (5 um pore size, Costar) at $1 \times 10^6$ cells/100 ul/well. The lower chambers were filled with 500 ul/well with GRS or fragment. After 30 minutes, 37° C. migration, migrated cells in the lower chamber were determined by fluorescence reading at Ex485/Em538.

Figure 12:
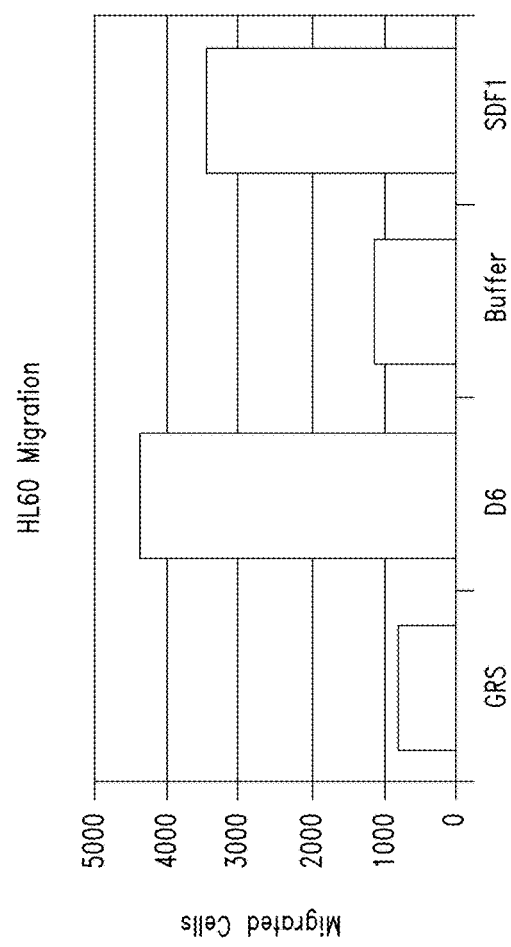
FIG. 12 shows that GlyRS fragment G6 induces migration of HL-60 promyelocytic leukemia cells.

The results of this study, as shown in FIG. 12, demonstrate that G6 can induce promyelocytic leukemia cell migration.

EXAMPLE 12

Figure 13:
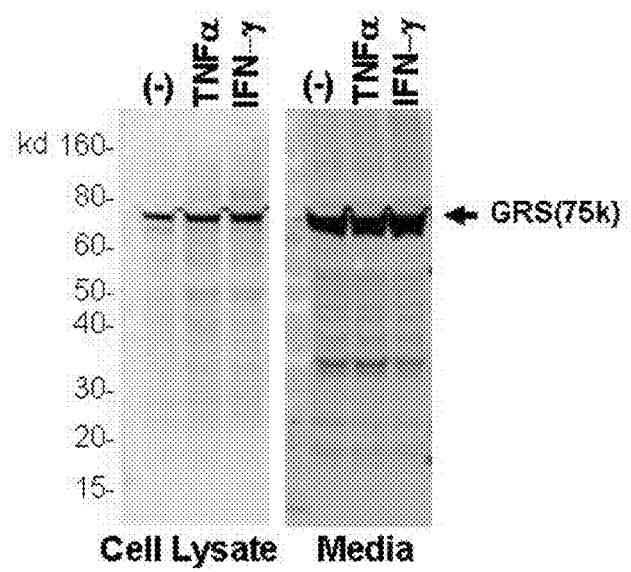
FIG. 13 shows that GlyRS was detected in both the cell lysate and media of mouse macrophages, indicating endogenous secretion of full-length GlyRS.

Secretion of Full-Length GlyRS and Fragments from RAW264.7 Mouse Leukaemic Macrophage Cells A. Endogenous Secretion of Full-Length GlyRS from RAW263.7 Cells RAW cells (mouse monocyte/macrophage cell line) were grown in 6 well tissue culture dishes until confluence. After two washes with PBS, cells were incubated 48 hours with serum-free DMEM (2 ml/flask) alone, or supplemented with TNFα or IFN-γ. The conditioned medium was collected and centrifuged at 20,000×G for 30 minutes at 4 C to remove cell debris. The supernatant was precipitated with TCA at 10% concentration for 20 minutes. After an acetone wash, the protein pellet was dissolved into SDS-sample buffer for SDS-PAGE. Mouse polyclonal antibody against human GRS (Abnova) detected GlyRS in both the cell lysate and media, indicating endogenous secretion of full-length GlyRS from mouse macrophages (FIG. 13).

Figure 14:
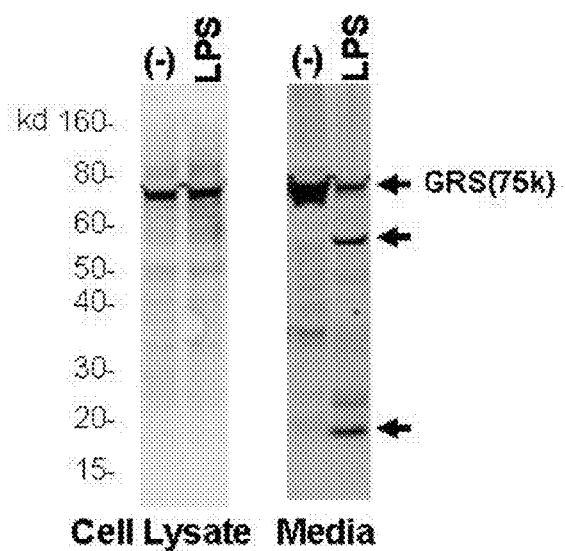
FIG. 14 shows that upon LPS treatment of mouse macrophages, specific fragments of GlyRS can be found in the secreted media but not in the cell lysate, indicating the creation and secretion of GlyRS fragments.

B. Full-Length and Fragments of GlyRS are Secreted from RAW264.7 Mouse Leukaemic Macrophage Cells Upon Treatment with Lipopolysaccharide RAW264.7 cells (mouse monocyte/macrophage cell line) were grown in 6 well tissue culture dishes until confluence. After two washes with PBS, cells were incubated 48 hours with serum-free DMEM (2 ml/flask) plus LPS 10 ng/ml. The conditioned medium was collected and centrifuged at 20,000×G for 30 minutes at 4 C to remove cell debris. The supernatant was precipitated with TCA at 10% concentration for 20 minutes. After an acetone wash, the protein pellet was dissolved into SDS-sample buffer for SDS-PAGE. Mouse polyclonal antibody against human GRS (Abnova) detected GlyRS in both the cell lysate and media. Upon LPS treatment, specific fragments of GlyRS were observed in the secreted media but not in the cell lysate, indicating the creation and secretion of these GlyRS fragments upon LPS treatment (FIG. 14).

Figure 15:
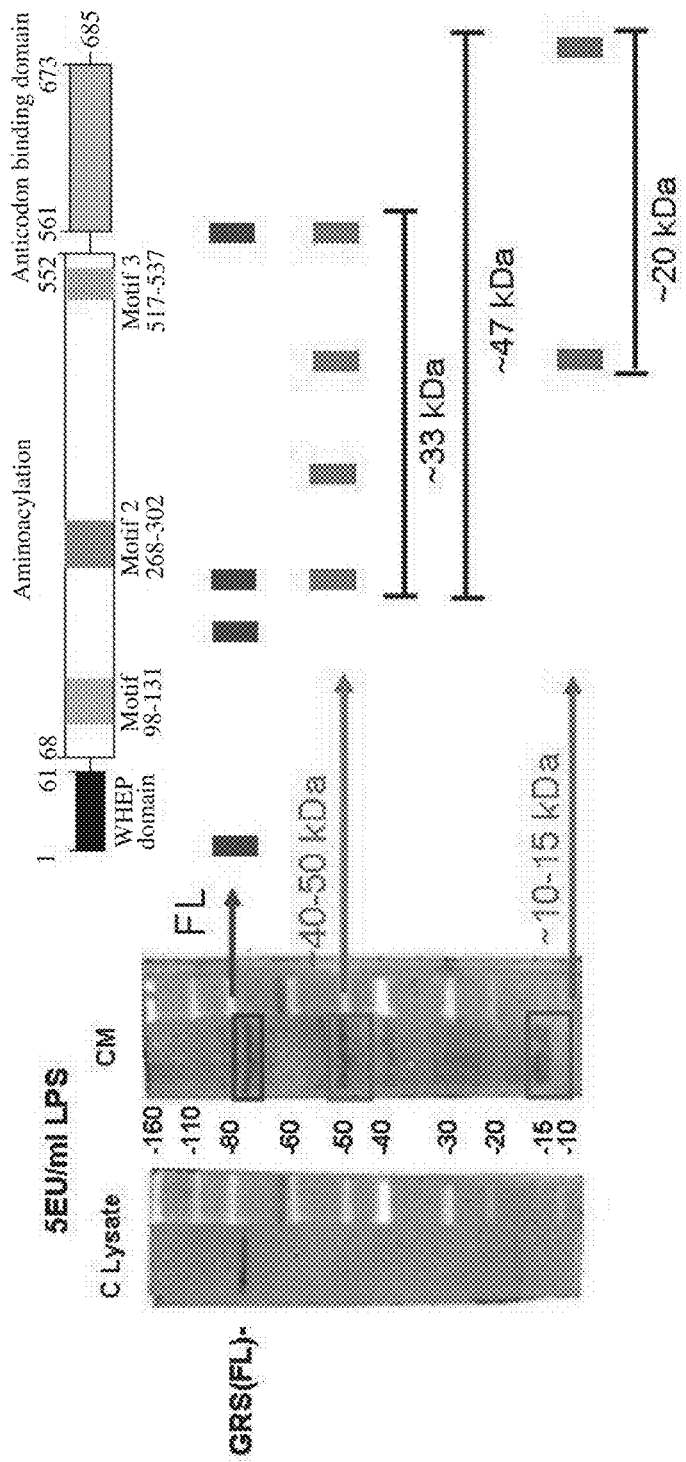
FIG. 15 shows the results of LC/MS/MS analysis to identify the portions of the full-length protein from which the fragments were generated following LPS treatment of mouse macrophages.

C. Identification of GlyRS Fragments Secreted from LPS-Treated Mouse Macrophage Cells by LC/MS/MS RAW246.7 cells (mouse monocyte/macrophage cell line) were grown in T25 flasks until confluence. Using the conditions outlined in above in B, cells were induced to secrete GlyRS fragments using LPS. The conditioned medium was collected and centrifuged at 20,000×G for 30 min at 4 C to remove cell debris. The supernatant (CM) was precipitated with TCA at 10% concentration for 20 minutes. After an acetone wash, the protein pellet was dissolved into SDS-sample buffer for SDS-PAGE. Individual fragments were excised from the SDS-PAGE gel and subjected to in-gel trypsin digestion followed by LC/MS/MS analysis to identify the portion of the full-length protein from which the fragment was generated (FIG. 15). Peptides identified from the fragment of ~40-50 kDa were located within the catalytic domain of the protein (see FIGS. 15, 16A) and based on theoretical molecular weight calculations, indicate this fragment likely represents a protein truncated at the N-terminus corresponding to amino acid residues from about 265-685 of GlyRS. Peptides identified from the fragment of ~15 kDa were located within the C-terminus of the protein (FIGS. 15, 16B) and based on theoretical molecular weight calculations, indicate this fragment likely represents the c-terminal portion of the protein corresponding to amino acid residues from about 483-685 of GlyRS As noted, the disclosure above is descriptive, illustrative and exemplary and is not to be taken as limiting the scope defined by the appended claims which follow.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A pharmaceutical composition, comprising a pharmaceutically-acceptable carrier and an isolated RNA polynucleotide having at least one modified nucleotide, wherein the isolated RNA polynucleotide encodes a glycyl-tRNA synthetase (GRS) polypeptide that is up to about 500 amino acids in length and comprises amino acid residues 367-438 of SEQ ID NO:1, or a GRS variant that comprises a sequence at least 95% identical to residues 367-438 of SEQ ID NO:1.

2. The pharmaceutical composition of claim 1, wherein the GRS polypeptide comprises amino acid residues 367-438 of SEQ ID NO:1.

3. The pharmaceutical composition of claim 1, wherein the GRS polypeptide comprises amino acid residues 214-438, 214-685, 239-685, 265-685, 311-685, or 333-685 of SEQ ID NO:1, or wherein the GRS variant comprises a sequence at least 95% identical to residues 214-438, 214-685, 239-685, 265-685, 311-685, or 333-685 of SEQ ID NO:1.

4. The pharmaceutical composition of claim 3, wherein the GRS polypeptide comprises amino acid residues 214-438, 214-685, 239-685, 265-685, 311-685, or 333-685 of SEQ ID NO:1.

5. The pharmaceutical composition of claim 1, wherein the GRS polypeptide or GRS variant is up to about 400 amino acids in length.

6. The pharmaceutical composition of claim 5, wherein the GRS polypeptide comprises amino acid residues 367-438 of SEQ ID NO:1.

7. The pharmaceutical composition of claim 5, wherein the GRS polypeptide comprises amino acid residues 214-438, 311-685, or 333-685 of SEQ ID NO:1, or wherein the GRS variant comprises a sequence at least 95% identical to residues 214-438, 311-685, or 333-685 of SEQ ID NO:1.

8. The pharmaceutical composition of claim 7, wherein the GRS polypeptide comprises amino acid residues 214-438, 311-685, or 333-685 of SEQ ID NO:1.

9. The pharmaceutical composition of claim 1, wherein the GRS polypeptide or GRS variant is up to about 300 amino acids in length.

10. The pharmaceutical composition of claim 9, wherein the GRS polypeptide comprises amino acid residues 367-438 of SEQ ID NO:1.

11. The pharmaceutical composition of claim 9, wherein the GRS polypeptide comprises amino acid residues 214-438 of SEQ ID NO:1, or wherein the GRS variant comprises a sequence at least 95% identical to residues 214-438 of SEQ ID NO:1.

12. The pharmaceutical composition of claim 11, wherein the GRS polypeptide comprises amino acid residues 214-438 of SEQ ID NO:1.

13. The pharmaceutical composition of claim 12, wherein the GRS polypeptide consists essentially of amino acid residues 214-438 of SEQ ID NO:1.

14. The pharmaceutical composition of claim 1, wherein the GRS polypeptide or GRS variant is up to about 200 amino acids in length.

15. The pharmaceutical composition of claim 14, wherein the GRS polypeptide comprises residues 367-438 of SEQ ID NO:1.

16. The pharmaceutical composition of claim 1, wherein the GRS polypeptide or GRS variant is up to about 100 amino acids in length.

17. The pharmaceutical composition of claim 16, wherein the GRS polypeptide comprises residues 367-438 of SEQ ID NO:1.

18. The pharmaceutical composition of claim 17, wherein the GRS polypeptide consists essentially of residues 367-438 of SEQ ID NO:1.

19. The pharmaceutical composition of claim 1, wherein the GRS polypeptide or GRS variant is fused to a heterologous fusion partner.

* * * * *

SEQUENCE LISTING

```
<160> NUMBER OF SEQ ID NOS: 11

<210> SEQ ID NO 1
<211> LENGTH: 685
<212> TYPE: PRT
<213> ORGANISM: Homo sapiens

<400> SEQUENCE: 1

Met Asp Gly Ala Gly Ala Glu Glu Val Leu Ala Pro Leu Arg Leu Ala
1               5                   10                  15

Val Arg Gln Gln Gly Asp Leu Val Arg Lys Leu Lys Glu Asp Lys Ala
            20                  25                  30

Pro Gln Val Asp Val Asp Lys Ala Val Ala Glu Leu Lys Ala Arg Lys
        35                  40                  45

Arg Val Leu Glu Ala Lys Glu Leu Ala Leu Gln Pro Lys Asp Asp Ile
    50                  55                  60

Val Asp Arg Ala Lys Met Glu Asp Thr Leu Lys Arg Arg Phe Phe Tyr
65                  70                  75                  80

Asp Gln Ala Phe Ala Ile Tyr Gly Gly Val Ser Gly Leu Tyr Asp Phe
                85                  90                  95

Gly Pro Val Gly Cys Ala Leu Lys Asn Asn Ile Ile Gln Thr Trp Arg
            100                 105                 110

Gln His Phe Ile Gln Glu Glu Gln Ile Leu Glu Ile Asp Cys Thr Met
        115                 120                 125

Leu Thr Pro Glu Pro Val Leu Lys Thr Ser Gly His Val Asp Lys Phe
    130                 135                 140

Ala Asp Phe Met Val Lys Asp Val Lys Asn Gly Glu Cys Phe Arg Ala
145                 150                 155                 160

Asp His Leu Leu Lys Ala His Leu Gln Lys Leu Met Ser Asp Lys Lys
                165                 170                 175

Cys Ser Val Glu Lys Lys Ser Glu Met Glu Ser Val Leu Ala Gln Leu
            180                 185                 190

Asp Asn Tyr Gly Gln Gln Glu Leu Ala Asp Leu Phe Val Asn Tyr Asn
        195                 200                 205

Val Lys Ser Pro Ile Thr Gly Asn Asp Leu Ser Pro Pro Val Ser Phe
    210                 215                 220

Asn Leu Met Phe Lys Thr Phe Ile Gly Pro Gly Gly Asn Met Pro Gly
225                 230                 235                 240

Tyr Leu Arg Pro Glu Thr Ala Gln Gly Ile Phe Leu Asn Phe Lys Arg
                245                 250                 255

Leu Leu Glu Phe Asn Gln Gly Lys Leu Pro Phe Ala Ala Ala Gln Ile
            260                 265                 270

Gly Asn Ser Phe Arg Asn Glu Ile Ser Pro Arg Ser Gly Leu Ile Arg
        275                 280                 285

Val Arg Glu Phe Thr Met Ala Glu Ile Glu His Phe Val Asp Pro Ser
    290                 295                 300

Glu Lys Asp His Pro Lys Phe Gln Asn Val Ala Asp Leu His Leu Tyr
305                 310                 315                 320

Leu Tyr Ser Ala Lys Ala Gln Val Ser Gly Gln Ser Ala Arg Lys Met
```

```
            325                 330                 335
Arg Leu Gly Asp Ala Val Glu Gln Gly Val Ile Asn Asn Thr Val Leu
            340                 345                 350
Gly Tyr Phe Ile Gly Arg Ile Tyr Leu Tyr Leu Thr Lys Val Gly Ile
            355                 360                 365
Ser Pro Asp Lys Leu Arg Phe Arg Gln His Met Glu Asn Glu Met Ala
            370                 375                 380
His Tyr Ala Cys Asp Cys Trp Asp Ala Glu Ser Lys Thr Ser Tyr Gly
385                 390                 395                 400
Trp Ile Glu Ile Val Gly Cys Ala Asp Arg Ser Cys Tyr Asp Leu Ser
                405                 410                 415
Cys His Ala Arg Ala Thr Lys Val Pro Leu Val Ala Glu Lys Pro Leu
            420                 425                 430
Lys Glu Pro Lys Thr Val Asn Val Val Gln Phe Glu Pro Ser Lys Gly
            435                 440                 445
Ala Ile Gly Lys Ala Tyr Lys Lys Asp Ala Lys Leu Val Met Glu Tyr
            450                 455                 460
Leu Ala Ile Cys Asp Glu Cys Tyr Ile Thr Glu Met Glu Met Leu Leu
465                 470                 475                 480
Asn Glu Lys Gly Glu Phe Thr Ile Glu Thr Glu Gly Lys Thr Phe Gln
                485                 490                 495
Leu Thr Lys Asp Met Ile Asn Val Lys Arg Phe Gln Lys Thr Leu Tyr
            500                 505                 510
Val Glu Glu Val Val Pro Asn Val Ile Glu Pro Ser Phe Gly Leu Gly
            515                 520                 525
Arg Ile Met Tyr Thr Val Phe Glu His Thr Phe His Val Arg Glu Gly
            530                 535                 540
Asp Glu Gln Arg Thr Phe Phe Ser Phe Pro Ala Val Val Ala Pro Phe
545                 550                 555                 560
Lys Cys Ser Val Leu Pro Leu Ser Gln Asn Gln Glu Phe Met Pro Phe
                565                 570                 575
Val Lys Glu Leu Ser Glu Ala Leu Thr Arg His Gly Val Ser His Lys
            580                 585                 590
Val Asp Asp Ser Ser Gly Ser Ile Gly Arg Arg Tyr Ala Arg Thr Asp
            595                 600                 605
Glu Ile Gly Val Ala Phe Gly Val Thr Ile Asp Phe Asp Thr Val Asn
            610                 615                 620
Lys Thr Pro His Thr Ala Thr Leu Arg Asp Arg Asp Ser Met Arg Gln
625                 630                 635                 640
Ile Arg Ala Glu Ile Ser Glu Leu Pro Ser Ile Val Gln Asp Leu Ala
                645                 650                 655
Asn Gly Asn Ile Thr Trp Ala Asp Val Glu Ala Arg Tyr Pro Leu Phe
            660                 665                 670
Glu Gly Gln Glu Thr Gly Lys Lys Glu Thr Ile Glu Glu
            675                 680                 685

<210> SEQ ID NO 2
<211> LENGTH: 2759
<212> TYPE: DNA
<213> ORGANISM: Homo sapiens

<400> SEQUENCE: 2
gtcactcgta taaaaccta  tgctttgaag  gttctcgtgt  gtctcggcct  gcaggtctcg      60
ctcagagctg tgtccctgaa  catccaccct  gctggggtgg  cttgacgcac  ttctgtgcaa     120
```

```
atctgttcgc tcgcaaccct acctacctct ctcccgaacc ggagaaaacc ttcggcgggg      180
tccttccggg ttttgtgtcg aatctgcggc ggcgacccgg cgccgcgtca cgcggtggtg      240
aatgtgcggc agcacgcgcg ccgcgtcgtt tacgcggcga tttcatcatg ctccgagccg      300
ggcggcgcgc gccgcttccg tcgccaccct ctctggacag cccagggccg caggctcatg      360
ccctctccgc gtccagtgct gcttagaggt gctcgcgccg ctctgctgct gctgctgccg      420 cccggctct  tagcccgacc ctcgctcctg ctccgccggt ccctcagcgc ggcctcctgc      480
cccccgatct ccttgcccgc cgccgcctcc cggagcagca tggacggcgc gggggctgag      540
gaggtgctgg cacctctgag gctagcagtg cgccagcagg gagatcttgt gcgaaaactc      600
aaagaagata agcaccccca gtagacgta  gacaaagcag tggctgagct caaagcccgc      660
aagagggttc tggaagcaaa ggagctggcg ttacagccca agatgatat  tgtagaccga      720 gcaaaaatgg aagataccct gaagaggagg ttttctatg  atcaagcttt tgctatttat      780
ggaggtgtta gtggtctgta tgactttggg ccagttggct gtgctttgaa gaacaatatt      840
attcagacct ggaggcagca ctttatccaa gaggaacaga tcctggagat cgattgcacc      900
atgctcaccc ctgagccagt tttaaagacc tctggccatg tagacaaatt tgctgacttc      960
atggtgaaag acgtaaaaaa tggagaatgt tttcgtgctg accatctatt aaaagctcat     1020
ttacagaaat tgatgtctga taagaagtgt tctgtcgaaa agaaatcaga aatggaaagt     1080
gttttggccc agcttgataa ctatggacag caagaacttg cggatctttt tgtgaactat     1140
aatgtaaaat ctcccattac tggaaatgat ctatcccctc cagtgtcttt taacttaatg     1200
ttcaagactt tcattgggcc tggaggaaac atgcctgggt acttgagacc agaaactgca     1260
caggggattt tcttgaattt caaacgactt ttggagttca accaaggaaa gttgcctttt     1320
gctgctgccc agattggaaa ttcttttaga aatgagatct cccctcgatc tggactgatc     1380
agagtcagag aattcacaat ggcagaaatt gagcactttg tagatcccag tgagaaagac     1440
caccccaagt tccagaatgt ggcagacctt cacctttatt tgtattcagc aaaagcccag     1500
gtcagcggac agtccgctcg gaaaatgcgc ctgggagatg ctgttgaaca gggtgtgatt     1560
aataacacag tattaggcta tttcattggc cgcatctacc tctacctcac gaaggttgga     1620
atatctccag ataaactccg cttccggcag cacatggaga atgagatggc ccattatgcc     1680
tgtgactgtt gggatgcaga atccaaaaca tcctacggtt ggattgagat tgttggatgt     1740
gctgatcgtt cctgttatga cctctcctgt catgcacgag ccaccaaagt cccacttgta     1800
gctgagaaac ctctgaaaga acccaaaaca gtcaatgttg ttcagtttga acccagtaag     1860
ggagcaattg gtaaggcata taagaaggat gcaaaactgg tgatggagta tcttgccatt     1920
tgtgatgagt gctacattac agaaatggag atgctgctga atgagaaagg ggaattcaca     1980
attgaaactg aagggaaaac atttcagtta acaaaagaca tgatcaatgt gaagagattc     2040
cagaaaacac tatatgtgga agaagttgtt ccgaatgtaa ttgaaccttc cttcggcctg     2100
ggtaggatca tgtatacggt atttgaacat acattccatg tacgagaagg agatgaacag     2160
agaacattct tcagtttccc tgctgtagtt gctccattca aatgttccgt cctcccactg     2220
agccaaaacc aggagttcat gccatttgtc aaggaattat cggaagccct gaccaggcat     2280
ggagtatctc acaaagtaga cgattcctct gggtcaatcg aaggcgcta  tgccaggact     2340 gatgagattg gcgtggcttt tggtgtcacc attgactttg acacagtgaa caagacccc       2400 cacactgcaa ctctgaggga ccgtgactca atgcggcaga taagagcaga gatctctgag     2460
```

-continued

```
ctgcccagca tagtccaaga cctagccaat ggcaacatca catgggctga tgtggaggcc    2520
aggtatcctc tgtttgaagg gcaagagact ggtaaaaaag agacaatcga ggaatgagga    2580
caattttgac aacttttgac cacttgcgct aataaaaaaa aaaaaaaact actcttatgt    2640
ccactttaca aaagaaaaca gcattgtgat tactcccagg gaccgtattt tatcttcagt    2700
ggctgcctga ttttacccccc acaattaaag ttgaaggaat cctgaacaaa aaaaaaaa     2759
```

<210> SEQ ID NO 3
<211> LENGTH: 17
<212> TYPE: PRT
<213> ORGANISM: Homo sapiens

<400> SEQUENCE: 3

Pro Gly Tyr Leu Arg Pro Glu Thr Ala Gln Gly Ile Phe Leu Asn Phe
1               5                   10                  15

Lys

<210> SEQ ID NO 4
<211> LENGTH: 16
<212> TYPE: PRT
<213> ORGANISM: Homo sapiens

<400> SEQUENCE: 4

Thr Gly Asn Asp Leu Ser Pro Pro Val Ser Phe Asn Leu Met Phe Lys
1               5                   10                  15

<210> SEQ ID NO 5
<211> LENGTH: 9
<212> TYPE: PRT
<213> ORGANISM: Homo sapiens

<400> SEQUENCE: 5

Asn Val Val Gln Phe Glu Pro Ser Lys
1               5

<210> SEQ ID NO 6
<211> LENGTH: 19
<212> TYPE: PRT
<213> ORGANISM: Homo sapiens

<400> SEQUENCE: 6

Leu Tyr Val Glu Glu Val Val Pro Asn Val Ile Glu Pro Ser Phe Gly
1               5                   10                  15

Leu Gly Arg

<210> SEQ ID NO 7
<211> LENGTH: 20
<212> TYPE: PRT
<213> ORGANISM: Homo sapiens

<400> SEQUENCE: 7

Ala Ile Tyr Gly Gly Val Ser Gly Leu Tyr Asp Phe Gly Pro Val Gly
1               5                   10                  15

Cys Ala Leu Lys
            20

<210> SEQ ID NO 8
<211> LENGTH: 15
<212> TYPE: PRT
<213> ORGANISM: Homo sapiens

<400> SEQUENCE: 8

```
Gln His Phe Ile Gln Glu Glu Gln Ile Leu Glu Ile Asp Cys Thr
1               5                   10                  15

<210> SEQ ID NO 9
<211> LENGTH: 11
<212> TYPE: PRT
<213> ORGANISM: Homo sapiens

<400> SEQUENCE: 9

Thr Val Asn Val Val Gln Phe Glu Pro Ser Lys
1               5                   10

<210> SEQ ID NO 10
<211> LENGTH: 685
<212> TYPE: PRT
<213> ORGANISM: Homo sapiens

<400> SEQUENCE: 10

Met Asp Gly Ala Gly Ala Glu Glu Val Leu Ala Pro Leu Arg Leu Ala
1               5                   10                  15

Val Arg Gln Gln Gly Asp Leu Val Arg Lys Leu Lys Glu Asp Lys Ala
                20                  25                  30

Pro Gln Val Asp Val Asp Lys Ala Val Ala Glu Leu Lys Ala Arg Lys
            35                  40                  45

Arg Val Leu Glu Ala Lys Glu Leu Ala Leu Gln Pro Lys Asp Asp Ile
        50                  55                  60

Val Asp Arg Ala Lys Met Glu Asp Thr Leu Lys Arg Arg Phe Phe Tyr
65                  70                  75                  80

Asp Gln Ala Phe Ala Ile Tyr Gly Gly Val Ser Gly Leu Tyr Asp Phe
                85                  90                  95

Gly Pro Val Gly Cys Ala Leu Lys Asn Asn Ile Ile Gln Thr Trp Arg
            100                 105                 110

Gln His Phe Ile Gln Glu Glu Gln Ile Leu Glu Ile Asp Cys Thr Met
        115                 120                 125

Leu Thr Pro Glu Pro Val Leu Lys Thr Ser Gly His Val Asp Lys Phe
    130                 135                 140

Ala Asp Phe Met Val Lys Asp Val Lys Asn Gly Glu Cys Phe Arg Ala
145                 150                 155                 160

Asp His Leu Leu Lys Ala His Leu Gln Lys Leu Met Ser Asp Lys Lys
                165                 170                 175

Cys Ser Val Glu Lys Lys Ser Glu Met Glu Ser Val Leu Ala Gln Leu
            180                 185                 190

Asp Asn Tyr Gly Gln Gln Glu Leu Ala Asp Leu Phe Val Asn Tyr Asn
        195                 200                 205

Val Lys Ser Pro Ile Thr Gly Asn Asp Leu Ser Pro Pro Val Ser Phe
    210                 215                 220

Asn Leu Met Phe Lys Thr Phe Ile Gly Pro Gly Gly Asn Met Pro Gly
225                 230                 235                 240

Tyr Leu Arg Pro Glu Thr Ala Gln Gly Ile Phe Leu Asn Phe Lys Arg
                245                 250                 255

Leu Leu Glu Phe Asn Gln Gly Lys Leu Pro Phe Ala Ala Ala Gln Ile
            260                 265                 270

Gly Asn Ser Phe Arg Asn Glu Ile Ser Pro Arg Ser Gly Leu Ile Arg
        275                 280                 285

Val Arg Glu Phe Thr Met Ala Glu Ile Glu His Phe Val Asp Pro Ser
    290                 295                 300
```

Glu Lys Asp His Pro Lys Phe Gln Asn Val Ala Asp Leu His Leu Tyr
305                 310                 315                 320

Leu Tyr Ser Ala Lys Ala Gln Val Ser Gly Gln Ser Ala Arg Lys Met
            325                 330                 335

Arg Leu Gly Asp Ala Val Glu Gln Gly Val Ile Asn Asn Thr Val Leu
            340                 345                 350

Gly Tyr Phe Ile Gly Arg Ile Tyr Leu Tyr Leu Thr Lys Val Gly Ile
            355                 360                 365

Ser Pro Asp Lys Leu Arg Phe Arg Gln His Met Glu Asn Glu Met Ala
370                 375                 380

His Tyr Ala Cys Asp Cys Trp Asp Ala Glu Ser Lys Thr Ser Tyr Gly
385                 390                 395                 400

Trp Ile Glu Ile Val Gly Cys Ala Asp Arg Ser Cys Tyr Asp Leu Ser
                405                 410                 415

Cys His Ala Arg Ala Thr Lys Val Pro Leu Val Ala Glu Lys Pro Leu
            420                 425                 430

Lys Glu Pro Lys Thr Val Asn Val Val Gln Phe Glu Pro Ser Lys Gly
            435                 440                 445

Ala Ile Gly Lys Ala Tyr Lys Lys Asp Ala Lys Leu Val Met Glu Tyr
450                 455                 460

Leu Ala Ile Cys Asp Glu Cys Tyr Ile Thr Glu Met Glu Met Leu Leu
465                 470                 475                 480

Asn Glu Lys Gly Glu Phe Thr Ile Glu Thr Glu Gly Lys Thr Phe Gln
                485                 490                 495

Leu Thr Lys Asp Met Ile Asn Val Lys Arg Phe Gln Lys Thr Leu Tyr
            500                 505                 510

Val Glu Glu Val Val Pro Asn Val Ile Glu Pro Ser Phe Gly Leu Gly
            515                 520                 525

Arg Ile Met Tyr Thr Val Phe Glu His Thr Phe His Val Arg Glu Gly
530                 535                 540

Asp Glu Gln Arg Thr Phe Phe Ser Phe Pro Ala Val Val Ala Pro Phe
545                 550                 555                 560

Lys Cys Ser Val Leu Pro Leu Ser Gln Asn Gln Glu Phe Met Pro Phe
                565                 570                 575

Val Lys Glu Leu Ser Glu Ala Leu Thr Arg His Gly Val Ser His Lys
            580                 585                 590

Val Asp Asp Ser Ser Gly Ser Ile Gly Arg Arg Tyr Ala Arg Thr Asp
            595                 600                 605

Glu Ile Gly Val Ala Phe Gly Val Thr Ile Asp Phe Asp Thr Val Asn
            610                 615                 620

Lys Thr Pro His Thr Ala Thr Leu Arg Asp Arg Asp Ser Met Arg Gln
625                 630                 635                 640

Ile Arg Ala Glu Ile Ser Glu Leu Pro Ser Ile Val Gln Asp Leu Ala
                645                 650                 655

Asn Gly Asn Ile Thr Trp Ala Asp Val Glu Ala Arg Tyr Pro Leu Phe
            660                 665                 670

Glu Gly Gln Glu Thr Gly Lys Lys Glu Thr Ile Glu Glu
            675                 680                 685

<210> SEQ ID NO 11
<211> LENGTH: 685
<212> TYPE: PRT
<213> ORGANISM: Homo sapiens

<400> SEQUENCE: 11

```
Met Asp Gly Ala Gly Ala Glu Val Leu Ala Pro Leu Arg Leu Ala
1               5                   10                  15
Val Arg Gln Gln Gly Asp Leu Val Arg Lys Leu Lys Glu Asp Lys Ala
            20                  25                  30
Pro Gln Val Asp Val Asp Lys Ala Val Ala Glu Leu Lys Ala Arg Lys
                35                  40                  45
Arg Val Leu Glu Ala Lys Glu Leu Ala Leu Gln Pro Lys Asp Asp Ile
        50                  55                  60
Val Asp Arg Ala Lys Met Glu Asp Thr Leu Lys Arg Arg Phe Phe Tyr
65                  70                  75                  80
Asp Gln Ala Phe Ala Ile Tyr Gly Val Ser Gly Leu Tyr Asp Phe
                    85                  90                  95
Gly Pro Val Gly Cys Ala Leu Lys Asn Asn Ile Ile Gln Thr Trp Arg
                100                 105                 110
Gln His Phe Ile Gln Glu Gln Ile Leu Glu Ile Asp Cys Thr Met
            115                 120                 125
Leu Thr Pro Glu Pro Val Leu Lys Thr Ser Gly His Val Asp Lys Phe
    130                 135                 140
Ala Asp Phe Met Val Lys Asp Val Lys Asn Gly Glu Cys Phe Arg Ala
145                 150                 155                 160
Asp His Leu Leu Lys Ala His Leu Gln Lys Leu Met Ser Asp Lys Lys
                165                 170                 175
Cys Ser Val Glu Lys Lys Ser Glu Met Glu Ser Val Leu Ala Gln Leu
            180                 185                 190
Asp Asn Tyr Gly Gln Gln Glu Leu Ala Asp Leu Phe Val Asn Tyr Asn
        195                 200                 205
Val Lys Ser Pro Ile Thr Gly Asn Asp Leu Ser Pro Val Ser Phe
    210                 215                 220
Asn Leu Met Phe Lys Thr Phe Ile Gly Pro Gly Gly Asn Met Pro Gly
225                 230                 235                 240
Tyr Leu Arg Pro Glu Thr Ala Gln Gly Ile Phe Leu Asn Phe Lys Arg
                245                 250                 255
Leu Leu Glu Phe Asn Gln Gly Lys Leu Pro Phe Ala Ala Ala Gln Ile
            260                 265                 270
Gly Asn Ser Phe Arg Asn Glu Ile Ser Pro Arg Ser Gly Leu Ile Arg
        275                 280                 285
Val Arg Glu Phe Thr Met Ala Glu Ile Glu His Phe Val Asp Pro Ser
    290                 295                 300
Glu Lys Asp His Pro Lys Phe Gln Asn Val Ala Asp Leu His Leu Tyr
305                 310                 315                 320
Leu Tyr Ser Ala Lys Ala Gln Val Ser Gly Gln Ser Ala Arg Lys Met
                325                 330                 335
Arg Leu Gly Asp Ala Val Glu Gln Gly Val Ile Asn Asn Thr Val Leu
            340                 345                 350
Gly Tyr Phe Ile Gly Arg Ile Tyr Leu Tyr Leu Thr Lys Val Gly Ile
        355                 360                 365
Ser Pro Asp Lys Leu Arg Phe Arg Gln His Met Glu Asn Glu Met Ala
    370                 375                 380
His Tyr Ala Cys Asp Cys Trp Asp Ala Glu Ser Lys Thr Ser Tyr Gly
385                 390                 395                 400
Trp Ile Glu Ile Val Gly Cys Ala Asp Arg Ser Cys Tyr Asp Leu Ser
                405                 410                 415
```

-continued

```
Cys His Ala Arg Ala Thr Lys Val Pro Leu Val Ala Glu Lys Pro Leu
            420                 425                 430

Lys Glu Pro Lys Thr Val Asn Val Val Gln Phe Glu Pro Ser Lys Gly
        435                 440                 445

Ala Ile Gly Lys Ala Tyr Lys Lys Asp Ala Lys Leu Val Met Glu Tyr
    450                 455                 460

Leu Ala Ile Cys Asp Glu Cys Tyr Ile Thr Glu Met Glu Met Leu Leu
465                 470                 475                 480

Asn Glu Lys Gly Glu Phe Thr Ile Glu Thr Glu Gly Lys Thr Phe Gln
                485                 490                 495

Leu Thr Lys Asp Met Ile Asn Val Lys Arg Phe Gln Lys Thr Leu Tyr
            500                 505                 510

Val Glu Glu Val Val Pro Asn Val Ile Glu Pro Ser Phe Gly Leu Gly
        515                 520                 525

Arg Ile Met Tyr Thr Val Phe Glu His Thr Phe His Val Arg Glu Gly
    530                 535                 540

Asp Glu Gln Arg Thr Phe Phe Ser Phe Pro Ala Val Val Ala Pro Phe
545                 550                 555                 560

Lys Cys Ser Val Leu Pro Leu Ser Gln Asn Gln Glu Phe Met Pro Phe
                565                 570                 575

Val Lys Glu Leu Ser Glu Ala Leu Thr Arg His Gly Val Ser His Lys
            580                 585                 590

Val Asp Asp Ser Ser Gly Ser Ile Gly Arg Arg Tyr Ala Arg Thr Asp
        595                 600                 605

Glu Ile Gly Val Ala Phe Gly Val Thr Ile Asp Phe Asp Thr Val Asn
    610                 615                 620

Lys Thr Pro His Thr Ala Thr Leu Arg Asp Arg Asp Ser Met Arg Gln
625                 630                 635                 640

Ile Arg Ala Glu Ile Ser Glu Leu Pro Ser Ile Val Gln Asp Leu Ala
                645                 650                 655

Asn Gly Asn Ile Thr Trp Ala Asp Val Glu Ala Arg Tyr Pro Leu Phe
            660                 665                 670

Glu Gly Gln Glu Thr Gly Lys Lys Glu Thr Ile Glu Glu
        675                 680                 685
```